US008753640B2

(12) United States Patent
Wu

(10) Patent No.: US 8,753,640 B2
(45) Date of Patent: *Jun. 17, 2014

(54) MIC-BINDING ANTIBODIES AND METHODS OF USE THEREOF

(75) Inventor: Jennifer D. Wu, Mt. Pleasant, SC (US)

(73) Assignee: University of Washington Through Its Center For Commercialization, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/483,809

(22) Filed: May 30, 2012

(65) Prior Publication Data

US 2012/0315287 A1 Dec. 13, 2012

Related U.S. Application Data

(60) Provisional application No. 61/491,706, filed on May 31, 2011, provisional application No. 61/511,310, filed on Jul. 25, 2011, provisional application No. 61/534,140, filed on Sep. 13, 2011.

(51) Int. Cl.
*A61K 38/00* (2006.01)

(52) U.S. Cl.
USPC .............. 424/174.1; 530/388.85; 530/388.15; 530/389.7

(58) Field of Classification Search
None
See application file for complete search history.

(56) References Cited

U.S. PATENT DOCUMENTS

| 6,852,318 | B1 | 2/2005 | Varner |
| 8,182,809 | B1 * | 5/2012 | Wu ............................ 424/130.1 |
| 2003/0105000 | A1 | 6/2003 | Pero et al. |
| 2007/0248607 | A1 | 10/2007 | Spies et al. |

OTHER PUBLICATIONS

Steinle et al (Proc Natl Acad Sci, 1998, 95:12510-12515).*
Padlan et al, (FASEB J, 1995, 9:133-139).*
Burgess et al (J Cell Biol, 1990, 111:2129-2138).*
Lazar et al (Mol Cell Biol, 1998, 8:1247-1252).*
Abaza et al., Journal of Protein Chemistry, 11(5):433-444 (1992). "Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin."
Burgess et al., the Journal of Cell Biology, 111:2129-2138 (1990). "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue."
Busche et al., Human Gene Therapy, 17:135-146 (2006). "Natural Killer Cell-Mediated Rejection of Experimental Human Lung Cancer by Genetic Overexpression of Major Histocompatibility Complex Class I Chain-Related Gene A."
Carayannopoulos et al., the Journal of Immunology, 169:4079-4083 (2002). "Cutting Edge: Murine UL16-Binding Protein-Like Transcript 1: A Newly Described Transcript Encoding a High-Affinity Ligand for Murine NKG2D."
Cerwenka et al., Immunity, 12:721-727 (2000). "Retinoic Acid Early Inducible Genes Define a Ligand Family for the Activating NKG2D Receptor in Mice."
Cerwenka et al., PNAS, 98(20):11521-11526 (2001). "Ectopic expression of retinoic acid early inducible-1 gene (RAE-1) permits natural killer cell-mediated rejection of a MHC class I-bearing tumor in vivo."
Cerwenka et al., Tissue Antigens, 61:335-343 (2003). "NKG2D ligands: unconventional MHC class I-like molecules exploited by viruses and cancer."
Colman, Research in Immunology, 145(1):33-36 (1994). "Effects of amino acid sequence changes on antibody-antigen interactions."
Diefenbach et al., Nature, 413:165-171 (2001). "Rae1 and H60 ligands of the NKG2D receptor stimulate tumour immunity."
Diefenbach et al., Eur. J. Immunol., 33:318-391 (2003). "A novel ligand for the NKG2D receptor activates NK cells and macrophages and induces tumor immunity."
Doubrovina et al., the Journal of Immunology, 171:6891-6899 (2003). "Evasion from NK Cell Immunity by MHC Class I Chain-Related Molecules Expressing Colon Adenocarcinoma."
Friese et al., Cancer Research, 63:8996-9006 (2003). "MICA/NKG2D-Mediated Immunogene Therapy of Experimental Gliomas."
Groh et al., Proc. Natl. Acad. Sci. USA, 96:6879-6884 (1999). "Broad tumor-associated expression and recognition by tumor-derived γδ T cells of MICA and MICB."
Groh et al., Nature, 419:734-738 (2002). "Tumour-derived soluble MIC ligands impair expression of NKG2D and T-cell activation."
Gura, Science, 278:1041-1042 (1997). "Systems for Identifying New Drugs Are Often Faulty."
Holdenrieder et al., Int. J. Cancer., 118:684-687 (2006). "Soluble MICA in malignant diseases."
Jinushi et al., Int. J. Cancer., 104:354-361 (2003). "Expression and Role of MICA and MICB in Human Hepatocellular Carcinomas and Their Regulation by Retinoic Acid."
Kaiser, Science, 313:1370 (2006). "First Pass at Cancer Genome Reveals Complex Landscape."
Long, Seminars in Cancer Biology, 12:57-61 (2002). "Tumor cell recognition by natural killer cells."
Marten et al., Int. J. Cancer, 119:2359-2365 (2006). "Soluble MIC is elevated in the serum of patients with pancreatic carcinoma diminishing γδ T cell cytotoxicity."
Raffaghello et al., Neoplasia, 6(5):558-568 (2004). "Downregulation and/or Release of NKG2D Ligands as Immune Evasion Strategy of Human Neuroblastoma."
Raulet, Nature Reviews Immunology, 3:781-790 (2003). "Roles of the NKG2D Immunoreceptor and Its Ligands."

(Continued)

*Primary Examiner* — Misook Yu
*Assistant Examiner* — Julie Wu
(74) *Attorney, Agent, or Firm* — Mark J. FitzGerald; Nixon Peabody, LLP

(57) ABSTRACT

The technology described herein relates to antibodies and/or polypeptides which bind to MIC and inhibit MIC shedding. Methods of using such antibodies and/or polypeptides for the treatment of cancer are also described herein.

20 Claims, 10 Drawing Sheets

(56) References Cited

OTHER PUBLICATIONS

Rudikoff et al., Proc. Natl. Acad. Sci. USA, 79:1979-1983 (1982). "Single amino acid substitution altering antigen-binding specificity."

Salih et al., the Journal of Immunology, 169:4098-4102 (2002). "Cutting Edge: Down-Regulation of MICA on Human Tumors by Proteolytic Shedding."

Smyth et la., JEM, 202(5):583-588 (2005). "NKG2D function protects the host from tumor initiation."

Vetter et al., J Invest Dermatol, 118:600-605 (2002). "Expression of Stress-induced MHC Class I Related Chain Molecules on Human Melanoma."

Waldhauer et al., Cancer Res, 68(15):6368-6376 (2008). "Tumor-Associated MICA Is Shed by ADAM Proteases."

Wu et al., the Journal of Clinical Investigation, 114(4):560-568 (2004). "Prevalent expression of the immunostimulatory MHC class I chain-related molecule is counteracted by shedding in prostate cancer."

Tzartos, S.J., Methods Mol Biol. ;66:55-66 (1996). "Epitope mapping by antibody competition. Methodology and Evaluation of the validity of the technique."

* cited by examiner

1A

1B

7A

7B

>ScFv - H9
MAQVQLQQSGAELVKP
GASVKLSCKTSGYTFSNYYM
SWLKQMPGQNIEWIGNIYGG
NGGTGYNQKFKGATLTVDK
SSSTAYMQLSSLTSEDSAVY
FCARGDLYAMDYWGQGTTVT
*VSSGGGGSGGGGSGGGGSDI*
VLTQSPSSMSASLGDRVTIT
CQASQDIGNNLIWFQQKPGK
SPRPMIYYATNLANGVPSRF
SGSGSGTSYSLTISSMEAED
AATYYCQQWSSNPYTFGGGT
KLEIKRAAA

Figure 9

> scFV-H9
atggcccaggtgcaactgcagcagtctggggctgagctggtgaagcct
M A Q V Q L Q Q S G A E L V K P
ggggcttcagtgaagttgtcctgcaaaacttctggttacaccttcagcaattactatatg
 G A S V K L S C K T S G Y T F S N Y Y M
agttggttgaagcagatgcctggacagaatattgagtggatcggaaacatttatggtgga
 S W L K Q M P G Q N I E W I G N I Y G G
aatggtggtactggctataatcagaagttcaagggcaaggccacactgacagtagacaaa
 N G G T G Y N Q K F K G K A T L T V D K
tcctccagcacagcctacatgcaactcagcagcctgacatctgaggactctgcggtctac
 S S S T A Y M Q L S S L T S E D S A V Y
ttctgtgcaagagggggacctctatgctatggactactggggccaagggaccacggtcacc
 F C A R G D L Y A M D Y W G Q G T T V T
gtctcctcaggtggaggcggttcaggcggaggtggctctggcggtggcggatcggacatc
 V S S G G G S G G G G S G G G S D I
gtgctgacccagtctccatcctccatgtctgcatctctgggagacagagtcactattact
 V L T Q S P S S M S A S L G D R V T I T
tgccaggcaagtcaggacattgggaataatttaatctggttccagcagaaaccagggaaa
 C Q A S Q D I G N N L I W F Q Q K P G K
tctcctaggcctatgatttattatgcaaccaacttggcaaatggggtcccatcaaggttc
 S P R P M I Y Y A T N L A N G V P S R F
agtggcagtgggtctgggacctcttactctctcacaatcagcagcatggaggctgaagat
 S G S G S G T S Y S L T I S S M E A E D
gctgccacttattactgccagcagtggagtagtaacccgtacacgttcggaggggggacc
 A A T Y Y C Q Q W S S N P Y T F G G G T
aagctggaaataaaacgggcggccgca
K L E I K R A A A

Figure 10

MIC-BINDING ANTIBODIES AND METHODS OF USE THEREOF

CROSS REFERENCE TO RELATED APPLICATIONS

This application claims benefit under 35 U.S.C. §119(e) of U.S. Provisional Application Nos. 61/491,706 filed May 31, 2011; 61/511,310 filed Jul. 25, 2011; and 61/534,140 filed Sep. 13, 2011, the contents of which are incorporated herein by reference in their entirety.

GOVERNMENT SUPPORT

This invention was made with federal funding under Grant Nos. W81XWH-06-1-0014, awarded by the Department of Defense, and 1K01CA116002 and 1R01CA149405 awarded by the National Institutes of Health. The U.S. government has certain rights in the invention.

SEQUENCE LISTING

The instant application contains a Sequence Listing which has been submitted in ASCII format via EFS-Web and is hereby incorporated by reference in its entirety. Said ASCII copy, created on May 22, 2012, is named 034186US.txt and is 12,122 bytes in size.

TECHNOLOGICAL FIELD

Embodiments of the technology described herein relate to antibodies and antigen-binding fragments thereof which bind a MIC polypeptide and inhibit MIC shedding. Also described herein are methods of treating cancer by administering the antibodies and antigen-binding portions thereof described herein.

BACKGROUND

Expression of murine NKG2D ligands on tumor cells has been shown to be effective in inducing natural killer cells (NK cells) to eliminate tumor cells (i.e. tumor rejection). In humans, the MHC class I chain-related molecule A (MICA) and MICB (generally termed as MIC) are the most investigated NKG2D ligands, which were proposed to play roles in tumor rejection. Expression of MIC on the tumor cell surface can markedly enhance the sensitivity of tumor cells to NK cells in vitro and has been shown to inhibit the growth of human gliomas or small lung carcinomas in experimental models. These studies suggest that NK cells can potentially eliminate MIC-positive tumor cells in cancer patients. However, as clinically observed, most of the human epithelial tumors are found to be MIC+ rather than MIC−. It has been shown that tumor-derived soluble MIC (sMIC), which occurs as a result of MIC shedding by MIC+ tumor cells is one of the factors causing the ineffectiveness of NKG2D-mediated immunity in cancer patients. sMIC is believed to induce down-modulation of NKG2D expression on systemic and tumor infiltrated NK and T cells and thus result in functional impairment of NK and T cells in MIC+ cancer patients. A reduction in the density of MIC expressed on the tumor cell surface due to MIC shedding from tumors is also one of the mechanisms for tumor evasion.

SUMMARY

Embodiments of the technology described herein are based on the discovery that an antibody and/or antigen-binding fragment thereof which binds a particular epitope (e.g. SEQ ID NO: 1) of a MIC polypeptide can inhibit MIC shedding. Also provided herein are complementarity determining regions (CDRs) comprised by antibodies or antigen-binding fragments thereof which bind the epitope of SEQ ID NO: 1 and inhibit MIC shedding. Methods of using these antibodies and antigen-binding portions thereof, including to treat certain cancers, are described herein.

Accordingly, in one embodiment, provided herein is an isolated antibody or antigen-binding portion thereof that specifically binds a MIC polypeptide, said antibody or antigen-binding portion thereof comprising heavy and light chain complementarity determining regions (CDRs): (a) a light chain CDR1 having the amino acid sequence of SEQ ID NO: 2; (b) a light chain CDR2 having the amino acid sequence of SEQ ID NO: 3; (c) a light chain CDR3 having the amino acid sequence of SEQ ID NO: 4; (d) a heavy chain CDR1 having the amino acid sequence of SEQ ID NO: 5; (e) a heavy chain CDR2 having the amino acid sequence of SEQ ID NO: 6; and (f) a heavy chain CDR3 having the amino acid sequence of SEQ ID NO: 7 or a conservative substitution variant of one or more of (a)-(e).

In some embodiments, the isolated antibody or antigen-binding portion thereof inhibits MIC shedding.

In some embodiments, the isolated antibody or antigen-binding portion thereof, when bound to MIC on the surface of a cell, does not decrease recognition of MIC by natural killer (NK) cells by more than 10%.

In some embodiments, the isolated antibody or antigen-binding portion thereof is selected from the group consisting of: an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, and a bispecific antibody.

In some embodiments, the isolated antibody or antigen-binding portion thereof comprises an scFV comprising the amino acid sequence of SEQ ID NO: 8.

In one aspect, the technology described herein relates to an isolated antibody or antigen-binding portion thereof that specifically binds an epitope comprising the amino acid sequence NGTYQT in a MIC polypeptide, said antibody or antigen-binding portion thereof comprising heavy chain CDRs having the amino acid sequences of: SEQ ID NO: 5, 6 and 7 or a conservative substitution variant of such amino acid sequence, said antibody or antigen-binding portion thereof inhibiting MIC shedding. In some embodiments, the isolated antibody or antigen-binding portion thereof comprises light chain CDRs having the amino acid sequences of SEQ ID NOs 2, 3, and 4 or a conservative substitution variant of such amino acid sequence. In some embodiments, the isolated antibody or antigen-binding portion thereof comprises a heavy chain comprising the amino acid sequence of SEQ ID NO: 09. In some embodiments, the isolated antibody or antigen-binding portion thereof comprises a light chain comprising the amino acid sequence of SEQ ID NO: 10.

In one aspect, the technology described herein relates to an isolated antibody or antigen-binding portion thereof that specifically binds an epitope comprising the amino acid sequence NGTYQT in a MIC polypeptide, said antibody or antigen-binding portion thereof comprising light chain CDRs having the amino acid sequences of SEQ ID NO: 2, 3 and 4 or a conservative substitution variant of such amino acid sequence, said antibody or antigen-binding portion thereof inhibiting MIC shedding. In some embodiments, the isolated antibody or antigen-binding portion thereof comprises heavy chain CDRs having the amino acid sequences of SEQ ID NOs 5, 6 and 7 or a conservative substitution variant of such amino acid sequence. In some embodiments, the isolated antibody or antigen-binding portion thereof comprises a light chain comprising the amino acid sequence of SEQ ID NO: 10. In some embodiments, the isolated antibody or antigen-binding portion thereof comprises a heavy chain comprising the amino acid sequence of SEQ ID NO: 09.

In one aspect, the technology described herein relates to an isolated antibody or antigen-binding portion thereof that competes with an antibody as described herein for binding to an epitope comprising the amino acid sequence NGTYQT in a MIC polypeptide.

In one aspect, the technology described herein relates to a pharmaceutical composition comprising an antibody or antigen-binding portion thereof as described herein and a pharmaceutically acceptable carrier.

In one aspect, the technology described herein relates to a method of inhibiting MIC shedding by a cell, the method comprising contacting the cell with an antibody antigen-binding portion thereof as described herein. In some embodiments, the cell is an MIC positive epithelial tumor cell or a MIC positive cell of a hematopoietic malignancy.

In one aspect, the technology described herein relates to a method of increasing surface MIC expression on a tumor cell, the method comprising contacting the cell with an antibody antigen-binding portion thereof as described herein. In some embodiments, the cell is a MIC positive epithelial tumor cell or a MIC positive cell of a hematopoietic malignancy.

In one aspect, the technology described herein relates to a method of treating a MIC positive epithelial cell tumor or a MIC positive hematopoietic malignancy in a subject, the method comprising administering an antibody or antigen binding portion thereof as described herein to the subject.

In one aspect, the technology described herein relates to a nucleic acid encoding an antibody or antigen-binding portion thereof as described herein.

In some embodiments, described herein is a method of enhancing NKG2D-mediated tumor cell killing, the method comprising contacting a tumor cell with an antibody or antigen-binding portion thereof as described herein. In some embodiments, the tumor cell is a MIC positive cell.

In some embodiments, described herein is a method of inhibiting tumor growth, the method comprising contacting a tumor cell with an antibody or antigen-binding portion thereof as described herein. In some embodiments, the tumor cell is a MIC positive cell.

BRIEF DESCRIPTION OF THE DRAWINGS

FIG. 1A is a schematic of the transgenic constructs. Expression of MICB or MICB.A2 was under the direction of the rat probasin promoter (−426 to +28 bp). Part (amino acid 215-274) of the α3 domain of MICB was replaced with the corresponding sequence of human HLA-A2 to generate the shedding-resistant membrane-restricted MICB.A216. FIG. 1B depicts the results of RT-PCR detection of specific expression of MICB or MICB.A2 in the mouse prostate lobes. AP, anterior prostate. DP, dorsal prostate. LP, leteral prostate. VP, ventral prostate. LV, liver. LU, lung. MU, muscle. SP, spleen.

FIG. 3A depicts the results of flow cytometry analyses of NKG2D expression on splenic NK (DX5+) cells from the 24-week cohorts of TRAMP-MICB.A2, TRAMP and wild type B6 mice. Cells were stained with the anti-NKG2D mAb CX5 in combination with DX5 and anti-CD3. FIG. 3B depicts the results of flow cytometry analyses of NKG2D expression on splenic CD8 T cells from the 24-week cohorts of TRAMP-MICB.A2, TRAMP and wild type B6 mice. Cells were stained with the anti-NKG2D mAb CX5 in combination with anti-CD8 and anti-CD3. *, significantly different ($p<0.05$) from wild-type B6 or TRAMP littermates. FIG. 3C depicts the results of cytotoxicity killing assay of splenocytes from TRAMP-MICB.A2 mice, which sustained NKG2D-dependent killing of tumor cells as those from wild-type B6 mice. Pooled splenocytes from 24-week-old TRAMP-MICB.A2 mice or B6 mice were used as effector cells against TC2-MICB target cells in a standard $^{51}$Cr release assay. Splenocytes:Targets=150:1. Anti-mouse NKG2D antibody C7 was used as the blocking antibody. FIG. 3D demonstrates that the depletion of NK or CD8 T cells in cohorts (n=5 per cohort) of TRAMP-MICB.A2 mice resulted in the increased prostate volume due to carcinoma development. ** denotes the development of PD carcinoma. Data in 3A, 3B and 3C represents three independent experiments.

FIG. 4A demonstrates increased prostate weight in the cohorts of 24-week-old TRAMP-MICB mice (n=12) in comparison to TRAMP littermate (n=13). FIG. 4B depicts representative demonstration of PD tumors (representative of five) and enlarged lymph nodes from the cohort of 24-week-old TRAMP-MICB mice and a WD tumor and lymph node from a TRAMP littermate that has no metastasis.

FIG. 5A depicts IHC demonstrating the pattern of MICB expression in TRAMP-MICB mice. Note the sustained levels of cell surface MICB expression of WD carcinomas and the loss of cell surface MICB expression in the PD carcinomas. Bar, 100 μm. FIG. 5B depicts the results of semiquantitative RT-PCR reveals comparable levels of MICB expression in PD and WD tumors at the mRNA level. FIG. 5C depicts ELISA measurement of serum levels of sMICB in the cohorts of 24-week TRAMP-MICB mice during carcinoma development. Note that development of PD carcinomas is associated with marked elevation of serum levels of sMICB. No sMICB was detected (only at background level) in the serum of TRAMP or TRAMP-MICB.A2 mice. *, $p<0.05$. , $p<0.01$. *, $p<0.001$. ns, not significant. FIG. 5D depicts splenic population of NK and CD8 T cells and NKG2D+ NK and NKG2D+ CD8 T cells in the cohorts of 24-week TRAMP-MICB, TRAMP, and wild-type B6mice. Development of PD carcinoma in TRAMP-MICB mice is associated with depletion of splenic DX5+ (NK) and NKG2D+ NK cell population but not of CD8 T cells. ***, $p<0.001$ in comparison to mice with WD tumors. FIG. 5E depicts a comparison of splenic DX5+ NK and DX5+ NKG2D+NK cell population in cohorts of TRAMP and TRAMP-MICB mice at 16-wk and 12-wk of age. *, $p<0.05$ in comparison to TRAMP mice. Data shown represent results from three independent assays.

FIG. 8A depicts the results of flow cytometry showing binding of scFv-H9 (not the negative control scFV-A1) to TRAMP-C2 (TC2)− MICA cells, but not to shedding-resistant (TC2)-MICA.M5 cells. No binding of the negative control scFv-A1 was observed on any cells. Filled profiles are rabbit IgG controls. FIG. 8B demonstrates that scFV-H9 inhibits shedding of MICA and MICB in transfected TC2 cells and MICA-positive human prostate cancer M12 cells. The first series represents cells treated with ScFv-A 1 and the second series represents cells treated with ScFv-H9. FIG. 8C demonstrates that treatment with scFv-H9 for 24 h increases surface MIC expression on M12 cells. FIG. 8D depicts the results of a 4-h cytotoxicity assay showing that scFv-H9 increases the killing of MICA-positive M12 cells (target) by NK92 cells (effector). M12 cells were pre-incubated with or without (control) scFV-H9, or the MICA blocking antibody 6D4.6 before used for NK-92 killing assay. Note that shedding of MICA in the control does not significantly affect the killing ability of NK cells in a 4h assay.

FIG. 9 depicts the amino acid sequence of scFV-H9 (SEQ ID NO: 8).

FIG. 10 depicts the amino acid sequence of scFV-H9 (SEQ ID NO: 8) and a nucleotide sequence encoding scFV-H9 (SEQ ID NO: 22).

DETAILED DESCRIPTION

Figure 1A:
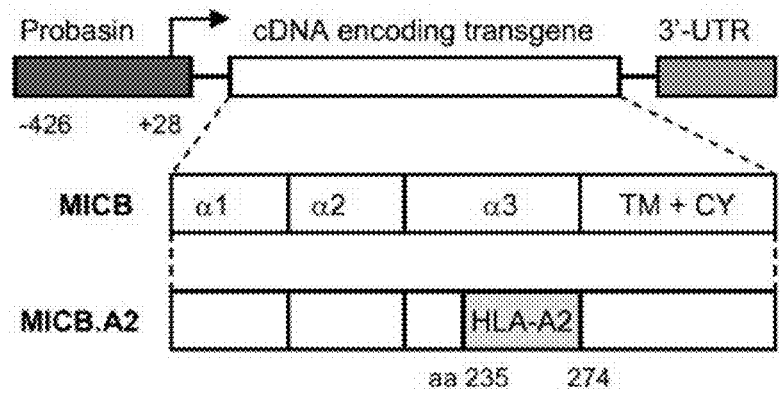
FIGS. 1A-1B depict construction of transgenic mice expressing the shedding-sensitive native MICB or the shedding-resistant membrane-bound mutant MICB.A2 in the prostate.

Embodiments of the technology described herein are based on the discovery that antibodies binding a particular epitope of the MIC protein inhibit MIC shedding. Described herein are CDRs of antibodies specific for this epitope of MIC. In some embodiments, such antibodies or antigen-binding fragments thereof can be used in the methods of treating epithelial cell tumors and/or hematopoietic malignancies.

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

The terms "decrease," "reduce," "reduced", "reduction", "decrease," and "inhibit" are all used herein generally to mean a decrease by a statistically significant amount relative to a reference. However, for avoidance of doubt, "reduce," "reduction" or "decrease" or "inhibit" typically means a decrease by at least 10% as compared to a reference level and can include, for example, a decrease by at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, up to and including, for example, the complete absence of the given entity or parameter as compared to the reference level, or any decrease between 10-99% as compared to the absence of a given treatment.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated." The terms "purified" or "substantially purified" refer to an isolated nucleic acid or polypeptide that is at least 95% by weight the subject nucleic acid or polypeptide, including, for example, at least 96%, at least 97%, at least 98%, at least 99% or more.

The terms "Kabat numbering", "Kabat definitions" and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof as described in Kabat et al. (1971) *Ann. NY Acad, Sci.* 190:382-391 and/or Kabat, E. A., et al. (1991) *Sequences of Proteins of Immunological Interest, Fifth Edition*, U.S. Department of Health and Human Services, NIH Publication No. 91-3242.

As used herein, an "epitope" can be formed both from contiguous amino acids, or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5, about 9, or about 8-10 amino acids in a unique spatial conformation. An "epitope" includes the unit of structure conventionally bound by an immunoglobulin VH/VL pair. Epitopes define the minimum binding site for an antibody, and thus represent the target of specificity of an antibody. In the case of a single domain antibody, an epitope represents the unit of structure bound by a variable domain in isolation. The terms "antigenic determinant" and "epitope" can also be used interchangeably herein. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics.

"Avidity" is the measure of the strength of binding between an antigen-binding molecule (such as an antibody or antibody fragment thereof described herein) and the pertinent antigen. Avidity is related to both the affinity between an antigenic determinant and its antigen binding site on the antigen-binding molecule, and the number of pertinent binding sites present on the antigen-binding molecule. Typically, antigen-binding proteins (such as an antibody or portion of an antibody as described herein) will bind to their cognate or specific antigen with a dissociation constant (KD of $10^{-5}$ to $10^{-12}$ moles/liter or less, such as $10^{-7}$ to $10^{-12}$ moles/liter or less, or $10^{-8}$ to $10^{-12}$ moles/liter (i.e., with an association constant (KA) of $10^5$ to $10^{12}$ liter/moles or more, such as $10^7$ to $10^{12}$ liter/moles or $10^8$ to $10^{12}$ liter/moles). Any KD value greater than $10^{-4}$ mol/liter (or any KA value lower than $10^4$ $M^{-1}$) is generally considered to indicate non-specific binding. The KD for biological interactions which are considered meaningful (e.g., specific) are typically in the range of $10^{-10}$ M (0.1 nM) to $10^{-5}$ M (10000 nM). The stronger an interaction, the lower is its KD. For example, a binding site on an antibody or portion thereof described herein will bind to the desired antigen with an affinity less than 500 nM, such as less than 200 nM, or less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as other techniques as mentioned herein.

Accordingly, as used herein, "selectively binds" or "specifically binds" refers to the ability of an anti-MIC-binding peptide (e.g., an antibody or portion thereof) described herein to bind to a target, such as a MIC molecule present on the cell-surface, with a KD $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. Specific binding can be influenced by, for example, the affinity and avidity of the polypeptide agent and the concentration of polypeptide agent. The person of ordinary skill in the art can determine appropriate conditions under which the polypeptide agents described herein selectively bind the targets using any suitable methods, such as titration of a polypeptide agent in a suitable cell binding assay. A polypeptide specifically bound to a target is not displaced by a non-similar competitor. In certain embodiments, an antibody or antigen-binding portion thereof is said to specifically bind an antigen when it preferentially recognizes its target antigen in a complex mixture of proteins and/or macromolecules.

As used herein the term "comprising" or "comprises" is used in reference to compositions, methods, and respective component(s) thereof, that are essential to the method or composition, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Other than in the operating examples, or where otherwise indicated, all numbers expressing quantities of ingredients or reaction conditions used herein should be understood as modified in all instances by the term "about." The term "about" when used in connection with percentages can mean±1%.

The term "statistically significant" or "significantly" refers to statistical significance and generally means a two standard deviation (2SD) difference, above or below a reference value. Additional definitions are provided in the text of individual sections below.

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); The ELISA guidebook (Methods in molecular biology 149) by Crowther J. R. (2000); Immunology by Werner Luttmann, published by Elsevier, 2006. Definitions of common terms in molecular biology can also be found in Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 0-56081-569-8) and Current Protocols in Protein Sciences 2009, Wiley Intersciences, Coligan et al., eds.

Unless otherwise stated, the present invention was performed using standard procedures, as described, for example in Methods in Enzymology, Volume 289: Solid-Phase Peptide Synthesis, J. N. Abelson, M. I. Simon, G. B. Fields (Editors), Academic Press; 1st edition (1997) (ISBN-13: 978-0121821906); Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

In some embodiments, the technology described herein relates to antibodies and/or polypeptides comprising an antigen-binding portion of an antibody which bind a MIC polypeptide. As used herein, the term "antibody" refers to immunoglobulin molecules and immunologically active portions of immunoglobulin molecules, i.e., molecules that contain an antigen binding site that immunospecifically bind an antigen. The term also refers to antibodies comprised of two immunoglobulin heavy chains and two immunoglobulin light chains as well as a variety of forms including full length antibodies and portions thereof; including, for example, an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody (dAb), a diabody, a multispecific antibody, a dual specific antibody, an anti-idiotypic antibody, a bispecific antibody, a functionally active epitope-binding fragment thereof, bifunctional hybrid antibodies (e.g., Lanzavecchia et al., Eur. J. Immunol. 17, 105 (1987)) and single chains (e.g., Huston et al., Proc. Natl. Acad. Sci. U.S.A., 85, 5879-5883 (1988) and Bird et al., Science 242, 423-426 (1988), which are incorporated herein by reference). (See, generally, Hood et al., Immunology, Benjamin, N.Y., 2ND ed. (1984), Harlow and Lane, Antibodies. A Laboratory Manual, Cold Spring Harbor Laboratory (1988) and Hunkapiller and Hood, Nature, 323, 15-16 (1986), which are incorporated herein by reference).

Each heavy chain is composed of a variable region of said heavy chain (abbreviated here as HCVR or VH) and a constant region of said heavy chain. The heavy chain constant region consists of three domains CH1, CH2 and CH3. Each light chain is composed of a variable region of said light chain (abbreviated here as LCVR or VL) and a constant region of said light chain. The light chain constant region consists of a CL domain. The VH and VL regions may be further divided into hypervariable regions referred to as complementarity-determining regions (CDRs) and interspersed with conserved regions referred to as framework regions (FR). Each VH and VL region thus consists of three CDRs and four FRs which are arranged from the N terminus to the C terminus in the following order: FR1, CDR1, FR2, CDR2, FR3, CDR3, FR4. This structure is well known to those skilled in the art.

As used herein, the term "CDR" refers to the complementarity determining region within antibody variable sequences. There are three CDRs in each of the variable regions of the heavy chain and of the light chain, which are designated CDR1, CDR2 and CDR3, for each of the variable regions. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Other boundaries defining CDRs overlapping with the Kabat CDRs have been described by Padlan (FASEB J. 9:133-139 (1995)) and MacCallum (J Mol Biol 262(5):732-45 (1996)) and Chothia (J. Mol. Biol. 196:901-917 (1987) and Nature 342:877-883 (1989)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat defined CDRs.

As used herein, the terms "proteins" and "polypeptides" are used interchangeably herein to designate a series of amino acid residues connected to the other by peptide bonds between the alpha-amino and carboxy groups of adjacent residues. The terms "protein", and "polypeptide", which are used interchangeably herein, refer to a polymer of protein amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to an encoded gene product and fragments thereof. Thus, exemplary polypeptides or proteins include gene products, naturally occurring proteins, homologs, orthologs, paralogs, fragments and other equivalents, variants, fragments, and analogs of the foregoing.

The terms "antigen-binding fragment" or "antigen-binding portion" of an antibody, used interchangeable herein, refer to one or more fragments of an antibody of the invention, said fragments) still having the binding affinities as defined above herein. Fragments of a complete antibody have been shown to be able to carry out the antigen-binding function of an antibody. In accordance with the term "antigen-binding portion" of an antibody, examples of binding fragments include (i) an Fab fragment, i.e. a monovalent fragment composed of the VL, VH, CL and CH1 domains; (ii) an F(ab')2 fragment, i.e. a bivalent fragment comprising two Fab fragments linked to one another in the hinge region via a disulfide bridge; (iii) an Fd fragment composed of the VH and CH1 domains; (iv) an Fv fragment composed of the FL and VH domains of a single arm of an antibody; and (v) a dAb fragment (Ward et al., (1989) Nature 341:544-546) consisting of a VH domain or of VH, CH1, CH2, DH3, or VH, CH2, CH3 (dAbs, or single domain antibodies, comprising only $V_L$ domains have also been shown to specifically bind to target eptiopes). Although the two domains of the Fv fragment, namely VL and VH, are encoded by separate genes, they may further be linked to one another using a synthetic linker, e.g. a poly-G4S amino acid sequence ('G4S' disclosed as SEQ ID NO: 20), and recombinant methods, making it possible to prepare them as a single protein chain in which the VL and VH regions combine in order to form monovalent molecules (known as single chain Fv (ScFv); see, for example, Bird et al. (1988) Science 242: 423-426; and Huston et al. (1988) *Proc. Natl. Acad. Sci. USA* 85:5879-5883). The term "antigen-binding portion" of an antibody is also intended to comprise such single chain antibodies. Other forms of single chain antibodies such as "diabodies" are likewise included here. Diabodies are bivalent, bispecific antibodies in which VH and VL domains are expressed on a single polypeptide chain, but using a linker which is too short for the two domains being able to combine on the same chain, thereby forcing said domains to pair with complementary domains of a different chain and to form two antigen-binding sites (see, for example, Holliger, R, et al. (1993) *Proc. Natl. Acad. Sci. USA* 90:64446448; Poljak, R. J, et al. (1994) *Structure* 2:1121-1123). An immunoglobulin constant domain refers to a heavy or light chain constant domain. Human IgG heavy chain and light chain constant domain amino acid sequences are known in the art.

Furthermore, an antibody as described herein or an antigen-binding portion thereof may be part of a larger immunoadhesion molecule formed by covalent or noncovalent association of said antibody or antibody portion with one or more further proteins or peptides. Relevant to such immunoadhesion molecules are the use of the streptavidin core region in order to prepare a tetrameric scFv molecule (Kipriyanov, S. M., et al. (1995) *Human Antibodies and Hybridomas* 6:93-101) and the use of a cystein residue, a marker peptide and a C-terminal polyhistidinyl, e.g. hexahistidinyl tag ('hexahistidinyl tag' disclosed as SEQ ID NO: 21) in order to produce bivalent and biotinylated scFv molecules (Kipriyanov, S. M., et al. (1994) *Mol. Immunol.* 31:10471058).

In some embodiments, the antibody and/or antigen-binding portion thereof described herein can be an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, a bispecific antibody, and a functionally active epitope-binding fragment thereof. In some embodiments, the polypeptide is a scFV comprising the amino acid sequence of SEQ ID NO:8.

As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retain the ability to specifically bind the target antigen (e.g. an epitope comprising the amino acid sequence NGTYQT (SEQ ID NO: 1) of a MIC polypeptide). Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. antigen-binding activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H).

Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class.

Particular conservative substitutions include, for example; Ala into Gly or into Ser; Arg into Lys; Asn into Gln or into H is; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments, the antibody and/or antigen-binding portion thereof described herein can be a variant of a sequence described herein, e.g. a conservative substitution variant of a polypeptide comprising the amino acid sequence of SEQ ID NO: 8. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity, e.g. antigen-specific binding activity for the relevant target polypeptide, e.g. a MIC polypeptide. A wide variety of PCR-based site-specific mutagenesis approaches are also known in the art and can be applied by the ordinarily skilled artisan. Examples of substitution variants include conservative substitution of amino acids, e.g. in a $V_H$ or $V_L$, domain, that do not alter the sequence of a CDR.

A variant amino acid or DNA sequence preferably is at least 90%, at least 91%, at least 92%, at least 93%, at least 94%, at least 95%, at least 96%, at least 97%, at least 98%, at least 99%, or more, identical to a native or reference sequence, e.g. SEQ ID NO:8. The degree of homology (percent identity) between a native and a mutant sequence can be determined, for example, by comparing the two sequences using freely available computer programs commonly employed for this purpose on the world wide web (e.g. BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by Walder et al. (Gene 42:133, 1986); Bauer et al. (Gene 37:73, 1985); Craik (BioTechniques, Jan.1985, 12-19); Smith et al. (Genetic Engineering: Principles and Methods, Plenum Press, 1981); and U.S. Pat. Nos. 4,518,584 and 4,737,462, which are herein incorporated by reference in their entireties.

Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

In some embodiments, the antibody or antigen-binding portion thereof is a fully human antibody. In some embodiments, the antibody or antigen-binding portion thereof is a humanized antibody. In some embodiments, the antibody or antigen-binding portion thereof is a chimeric antibody. In some embodiments, the antibody or antigen-binding portion thereof is a recombinant polypeptide.

The term "human antibody" refers to antibodies whose variable and constant regions correspond to or are derived from immunoglobulin sequences of the human germ line, as described, for example, by Kabat et al. (see Kabat, et al. (1991) *Sequences of Proteins of Immunological Interest, Fifth Edition*, U.S. Department of Health and Human Services, NIH Publication No. 91-3242). However, the human antibodies can contain amino acid residues not encoded by human germ line immunoglobulin sequences (for example mutations which have been introduced by random or site-specific mutagenesis in vitro or by somatic mutation in vivo), for example in the CDRs, and in particular in CDR3. Recombinant human antibodies of the invention have variable regions and may also contain constant regions derived from immunoglobulin sequences of the human germ line (see Kabat, E. A., et al. (1991) *Sequences of Proteins of Immunological Interest, Fifth Edition*, U.S. Department of Health and Human Services, NIH Publication No. 91-3242). According to particular embodiments, however, such recombinant human antibodies are subjected to in-vitro mutagenesis (or to a somatic in-vivo mutagenesis, if an animal is used which is transgenic due to human Ig sequences) so that the amino acid sequences of the VH and VL regions of the recombinant antibodies are sequences which although related to or derived from VH and VL sequences of the human germ line, do not naturally exist in vivo within the human antibody germ line repertoire. According to particular embodiments, recombinant antibodies of this kind are the result of selective mutagenesis or back mutation or of both. Preferably, mutagenesis leads to an affinity to the target which is greater, and/or an affinity to non-target structures which is smaller than that of the parent antibody.

The term "chimeric antibody" refers to antibodies which contain sequences for the variable region of the heavy and light chains from one species and constant region sequences from another species, such as antibodies having murine heavy and light chain variable regions linked to human constant regions. Humanized antibodies have variable region framework residues substantially from a human antibody (termed an acceptor antibody) and complementarity determining regions substantially from a non-human antibody, e.g. a mouse-antibody, (referred to as the donor immunoglobulin). See, Queen et al., *Proc Natl Acad Sci USA* 86:10029-10033 (1989) and WO 90/07861, U.S. Pat. Nos. 5,693,762, 5,693, 761, 5,585,089, 5,530,101 and Winter, U.S. Pat. No. 5,225, 539, which are herein incorporated by reference in their entirety. The constant region(s), if present, are also substantially or entirely from a human immunoglobulin. The human variable domains are usually chosen from human antibodies whose framework sequences exhibit a high degree of sequence identity with the (murine) variable region domains from which the CDRs were derived. The heavy and light chain variable region framework residues can be substantially similar to a region of the same or different human antibody sequences. The human antibody sequences can be the sequences of naturally occurring human antibodies or can be consensus sequences of several human antibodies. See Carter et al., WO 92/22653, which is herein incorporated by reference in its entirety.

In some embodiments, described herein is an isolated antibody or antigen-binding portion thereof that specifically binds a MIC polypeptide, said antibody or antigen-binding portion thereof comprising heavy and light chain complementarity determining regions (CDRs): (a) a light chain CDR1 having the amino acid sequence of SEQ ID NO: 2; (b) a light chain CDR2 having the amino acid sequence of SEQ ID NO: 3; (c) a light chain CDR3 having the amino acid sequence of SEQ ID NO: 4; (d) a heavy chain CDR1 having the amino acid sequence of SEQ ID NO: 5; (e) a heavy chain CDR2 having the amino acid sequence of SEQ ID NO: 6; and (f) a heavy chain CDR3 having the amino acid sequence of SEQ ID NO: 7 or a conservative substitution variant of one or more of (a)-(e).

As used herein, the term "conservative substitution variant" as applied to a CDR refers to a variant CDR in which a given sequence differs from the corresponding CDR of the original reference polypeptide by having no more than two conservative amino acid substitutions within that CDR. That is, a given CDR of a conservative substitution variant can vary from the CDR of the original reference polypeptide by having 1 conservative substitution or by having 2 conservative substitutions. A conservative substitution variant of an antibody or antigen-binding portion thereof can have 1 or more CDRs that differ from the original reference polypeptide; e.g. 1 CDR can vary, 2 CDRs can vary, 3 CDRs can vary, 4 CDRs can vary, 5 CDRs can vary, or 6 CDRs can vary. In some embodiments, only 1 CDR varies, only 2 CDRs vary, only 3 CDRs vary, only 4 CDRs vary, or only 5 CDRs vary.

In some embodiments, the antibody or polypeptide comprising an antigen-binding fragment of an antibody described herein comprises one or more CDRs, e.g. 1 CDR, 2 CDRs, 3 CDRs, 4 CDRs, 5 CDRs, or 6 CDRs, selected from the group consisting of (a) a light chain CDR1 having the amino acid sequence of SEQ ID NO: 2; (b) a light chain CDR2 having the amino acid sequence of SEQ ID NO: 3; (c) a light chain CDR3 having the amino acid sequence of SEQ ID NO: 4; (d) a heavy chain CDR1 having the amino acid sequence of SEQ ID NO: 5; (e) a heavy chain CDR2 having the amino acid sequence of SEQ ID NO: 6; and (f) a heavy chain CDR3 having the amino acid sequence of SEQ ID NO: 7. In some embodiments, the antibody or polypeptide comprising an antigen-binding fragment of an antibody described herein comprises a heavy chain or a portion thereof, comprising one or more CDRs, e.g., 1 CDR, 2 CDRs, or 3 CDRs selected from the group consisting of a heavy chain CDR1 having the amino acid sequence of SEQ ID NO: 5; a heavy chain CDR2 having the amino acid sequence of SEQ ID NO: 6; and a heavy chain CDR3 having the amino acid sequence of SEQ ID NO: 7. In some embodiments, the antibody or polypeptide comprising an antigen-binding fragment of an antibody described herein comprises a light chain or a portion thereof, comprising one or more CDRs, e.g., 1 CDR, 2 CDRs, or 3 CDRs selected from the group consisting of a light chain CDR1 having the amino acid sequence of SEQ ID NO: 2; a light chain CDR2 having the amino acid sequence of SEQ ID NO: 3; a light chain CDR3 having the amino acid sequence of SEQ ID NO: 4.

In some embodiments, an isolated antibody or antigen-binding portion thereof described herein comprises a sequence wherein at least one CDRs of that sequence has at least 90% sequence identity, e.g. 90%, 91%, 92%, 93%, 94%, 95%, 96%, 97%, 98%, 99% or greater sequence identity with a CDR selected from the group consisting of (a) a light chain CDR1 having the amino acid sequence of SEQ ID NO: 2; (b) a light chain CDR2 having the amino acid sequence of SEQ ID NO: 3; (c) a light chain CDR3 having the amino acid sequence of SEQ ID NO: 4; (d) a heavy chain CDR1 having the amino acid sequence of SEQ ID NO: 5; (e) a heavy chain CDR2 having the amino acid sequence of SEQ ID NO: 6; and (f) a heavy chain CDR3 having the amino acid sequence of SEQ ID NO: 7. In some embodiments, an isolated antibody or antigen-binding portion thereof described herein comprises a sequence wherein at least one CDRs of that sequence has at least 95% sequence identity, e.g. 95%, 96%, 97%, 98%, 99% or greater sequence identity with a CDR selected from the group consisting of (a) a light chain CDR1 having the amino acid sequence of SEQ ID NO: 2; (b) a light chain CDR2 having the amino acid sequence of SEQ ID NO: 3; (c) a light chain CDR3 having the amino acid sequence of SEQ ID NO: 4; (d) a heavy chain CDR1 having the amino acid sequence of SEQ ID NO: 5; (e) a heavy chain CDR2 having the amino acid sequence of SEQ ID NO: 6; and (f) a heavy chain CDR3 having the amino acid sequence of SEQ ID NO: 7. In some embodiments, an isolated antibody or antigen-binding portion thereof described herein comprises a sequence wherein at least one CDRs of that sequence has at least 90% sequence identity, e.g. 90%, 91%, 92%, 93%, 94%, 95%, 96%, 97%, 98%, 99% or greater sequence identity with SEQ ID NO: 8. In some embodiments, an isolated antibody or antigen-binding portion thereof described herein comprises a sequence wherein at least one CDRs of that sequence has at least 95% sequence identity, e.g. 95%, 96%, 97%, 98%, 99% or greater sequence identity with SEQ ID NO: 8.

In some embodiments, described herein is an isolated antibody or antigen-binding portion thereof that specifically binds an epitope comprising the amino acid sequence NGTYQT (SEQ ID NO: 1) in a MIC polypeptide, the antibody or antigen-binding portion thereof comprising heavy chain CDRs having the amino acid sequences of SEQ ID NO: 5, 6, and 7 or a conservative substitution variant of such amino acid sequence, said antibody or antigen-binding portion thereof inhibiting MIC shedding. In some embodiments, the isolated antibody or antigen-binding portion thereof can comprise light chain CDRs having the amino acid sequences of SEQ ID NOs 2, 3, and 4 or a conservative substitution variant of such amino acid sequence. In some embodiments, the isolated antibody or antigen-binding portion thereof can comprise a heavy chain comprising the amino acid sequence of SEQ ID NO: 09. In some embodiments, the isolated antibody or antigen-binding portion thereof can comprise a light chain comprising the amino acid sequence of SEQ ID NO: 10.

In some embodiments, described herein is an isolated antibody or antigen-binding portion thereof that specifically binds an epitope comprising the amino acid sequence NGTYQT (SEQ ID NO: 1) in a MIC polypeptide, said antibody or antigen-binding portion thereof comprising light chain CDRs having the amino acid sequences of SEQ ID NO: 2, 3, and 4 or a conservative substitution variant of such amino acid sequence, said antibody or antigen-binding portion thereof inhibiting MIC shedding. In some embodiments, the isolated antibody or antigen-binding portion thereof can comprise heavy chain CDRs having the amino acid sequences of SEQ ID NOs 5, 6, and 7 or a conservative substitution variant of such amino acid sequence. In some embodiments, the isolated antibody or antigen-binding portion thereof can comprise a light chain comprising the amino acid sequence of SEQ ID NO: 10. In some embodiments, the isolated antibody or antigen-binding portion thereof can comprise a heavy chain comprising the amino acid sequence of SEQ ID NO: 09.

In embodiments wherein an antibody as described herein comprises at least one CDR which is not identical to the sequence of SEQ ID NOs: 2-7, the amino acid sequence of that at least one CDR can be selected by methods well known to one of skill in the art. For example, Fujii, 2004, "Antibody affinity maturation by random mutagenesis" in Methods in Molecular Biology: Antibody Engineering 248: 345-349 (incorporated by reference herein in its entirety), particularly at FIG. 2 and Section 3.3, describes methods of generating a library for any CDR of interest. This allows one of ordinary skill in the art to identify alternative CDRs, including conservative substitution variants of the specific CDR sequences described herein, which, when present in an antibody or antigen-binding fragment thereof as described herein, will result in an antigen or antigen-binding fragment thereof which will bind a MIC polypeptide. In some embodiments, the antibody or antigen-binding fragment thereof can bind an epitope comprising the amino acid sequence NGTYQT (SEQ ID NO: 1). In some embodiments, the antibody or antigen-binding fragment thereof can inhibit MIC shedding. The method described in Fujii et al. also permits one of ordinary skill in the art to screen for a light chain sequence which will give the desired binding behavior when combined with a known heavy chain fragment and vice versa.

In some embodiments, described herein is an isolated antibody or antigen-binding portion thereof that competes with a second antibody or antigen-binding portion thereof (said second antibody or antigen-binding portion thereof comprising heavy and light chain complementarity determining regions (CDRs) comprising: (a) a light chain CDR1 having the amino acid sequence of SEQ ID NO: 2; (b) a light chain CDR2 having the amino acid sequence of SEQ ID NO: 3; (c) a light chain CDR3 having the amino acid sequence of SEQ ID NO: 4; (d) a heavy chain CDR1 having the amino acid sequence of SEQ ID NO: 5; (e) a heavy chain CDR2 having the amino acid sequence of SEQ ID NO: 6; and (f) a heavy chain CDR3 having the amino acid sequence of SEQ ID NO: 7 for binding to an epitope comprising the amino acid sequence NGTYQT (SEQ ID NO: 1) in a MIC polypeptide.

In some embodiments, an antibody or antigen-binding portion thereof as described herein which binds to a MIC polypeptide with a dissociation constant (KD) of $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. In some embodiments, an isolated antibody or antigen-binding portion thereof described herein binds a MIC polypeptide with a dissociation constant (KD) of from about $10^{-5}$ M to $10^{-6}$ M. In some embodiments, an isolated antibody or antigen-binding portion thereof described herein binds a MIC polypeptide with a dissociation constant (KD) of from about $10^{-6}$ M to $10^{-7}$ M. In some embodiments, an isolated antibody or antigen-binding portion thereof described herein binds a MIC polypeptide with a dissociation constant (KD) of from about $10^{-7}$ M to $10^{-8}$ M. In some embodiments, an isolated antibody or antigen-binding portion thereof described herein binds a MIC polypeptide with a dissociation constant (KD) of from about $10^{-8}$ M to $10^{-9}$ M. In some embodiments, an isolated antibody or antigen-binding portion thereof described herein binds a MIC polypeptide with a dissociation constant (KD) of from about $10^{-9}$ M to $10^{-10}$ M. In some embodiments, an isolated antibody or antigen-binding portion thereof described herein binds a MIC polypeptide with a dissociation constant (KD) of from about $10^{-10}$ M to $10^{-11}$ M. In some embodiments, an isolated antibody or antigen-binding portion thereof described herein binds a MIC polypeptide with a dissociation constant (KD) of from about $10^{-11}$ M to $10^{-12}$ M. In some embodiments, an isolated antibody or antigen-binding portion thereof described herein binds a MIC polypeptide with a dissociation constant (KD) of less than $10^{-12}$ M.

In some embodiments, an isolated antibody or antigen-binding portion thereof described herein inhibits MIC shedding. MIC shedding can be measured by any method known in the art. Examples are provided herein in the Examples and in U.S. patent application Ser. No. 12/555,149; which is incorporated by reference herein in its entirety. Briefly, cells are contacted with an antibody specific for the ectodomain of a MIC polypeptide and which contains a detectable label and then analyzed by flow cytometry. A higher level of antibody detected on the surface of the cells treated with an antibody or antigen-binding portion thereof as described herein that binds an epitope comprising amino acids NGTYQT (SEQ ID NO:1) of a MIC polypeptide can indicate inhibition of MIC shedding. Alternatively, a decrease in circulating MIC as detected, e.g. by immunoprecipitation for blood, serum, or plasma would also provide a measure of MIC shedding in an animal or subject with a MIC positive tumor. Antibodies suitable for use in such assays are available commercially e.g. Cat No. #10759-H08H from Sino Biological; Beijing, China. In some embodiments, the antibody for detection of MIC is not detectably labeled, and a detectably labeled secondary antibody is used.

In some embodiments, an isolated antibody or antigen-binding portion thereof described herein specifically binds a MIC polypeptide. In some embodiments, an isolated antibody or antigen-binding portion thereof described herein specifically binds the epitope comprising the amino acid sequence NGTYQT (SEQ ID NO: 1). In some embodiments, the epitope comprising the amino acid sequence NGTYQT (SEQ ID NO: 1) is comprised by the α3 ectodomain of a MIC polypeptide. In some embodiments, an isolated antibody or antigen-binding portion thereof described herein physically contacts at least one amino acid of the epitope comprising the amino acid sequence NGTYQT (SEQ ID NO: 1) which is comprised by the α3 ectodomain of a MIC polypeptide. Binding of an antibody or polypeptide to an epitope can be determined by any method known in the art, including, for example, ELISA, pull-down, immunoassay, yeast-two hybrid, electrophoretic mobility shift assays, and the like.

Major Histocompatibility Complex class I chain-related (MIC) polypeptides are surface transmembrane proteins. The presence of a MIC polypeptide on the cell surface can signal the immune receptor NKG2D for tumor immune destruction, typically by natural killer cells (NK cells) and cytotoxic T cells (CTLs). However, in many tumors, MIC is shed from the tumor surface by interaction with ERp5 with the amino acid sequence of SEQ ID NO:1, resulting in decreased host immunity against the tumor cell and promotes tumor evasion and progression. MIC polypeptides include, but are not limited to the human MICA (e.g. NCBI Ref Seqs NP_000238 and 001170990) and human MICB (e.g. NCBI Ref Seq: NP_005922). In some embodiments, a MIC polypeptide can comprise MICA. In some embodiments, a MIC polypeptide can comprise MICB.

As used herein, the phrase "region in the alpha-3 ectodomain of MIC" comprises at least the amino acid sequence NGTYQT (SEQ ID NO: 1) sequence necessary for MIC interaction with ERp5 polypeptide. The term refers generally to that region that is necessary for shedding of MIC from a tumor cell. In one embodiment, the region that is necessary for MIC shedding comprises or alternatively, consists essentially of, the amino acid sequence TQQWGDVLPDGNGTYQTWVATR (SEQ ID NO: 14). In another embodiment, the region that is necessary for MIC shedding comprises, or alternatively, consists essentially of, the amino acid sequence NGTYQT (SEQ ID NO: 1). In another embodiment, the region comprises the amino acid sequence QTWVATR (SEQ ID NO: 11), YQTWVATR (SEQ ID NO: 12) or TWVA (SEQ ID NO: 13). As used herein, the term "MIC peptide cleavage site" refers to a sequence of the alpha-3 ectodomain of a MIC polypeptide that is sufficient to direct cleavage in an ERp5-dependent manner. At a minimum, while the peptide is not necessarily cleaved at the amino acid sequence NGTYQT (SEQ ID NO: 1), a MIC cleavage site peptide will comprise an NGTYQT (SEQ ID NO: 1) sequence, e.g., in the context of a larger peptide, e.g., a peptide comprising sequence identified as critical for MIC shedding.

In some embodiments, an isolated antibody or antigen-binding portion thereof described herein increases cell surface MIC expression, which can be measured, by methods known in the art. By way of non-limiting example, an assay for detecting surface MIC expression is described in U.S. patent application Ser. No. 12/555,194. Briefly, cells are trypsinized, blocked with anti-mouse CD16/32 (eBiosciences, San Diego, Calif.), and incubated with anti-MICA/B mAb 6D4.6 or anti-MICB MAB1599 (R&D systems) or anti-pan-RAE-1 mAb17582 (R&D systems) followed by a PE-conjugated secondary reagent, followed by flow cytometry analysis.

In some embodiments, an isolated antibody or antigen-binding portion thereof, as described herein, does not decrease recognition of MIC by natural killer (NK) cells by more than 10%., e.g. by no more than 10%, by no more than 9%, by no more than 8%, by no more than 7%, or less. NK-mediated killing can be determined by methods known in the art. By way of non-limiting example, a 4-h cytotoxicity assay can be used as described herein. Briefly, target cells can be pre-incubated with or without control antibody and a MIC-binding antibody or polypeptide before the cells are used in a NK-92 killing assay. Killing assays utilizing NK-92 are well known in the art and are described, for example in Gong et al. Leukemia 1994; 8:652-658; which is incorporated by reference herein in its entirety. Briefly, a known quantity of living target cells is incubated with NK-92 cells and the number of living cells, or the increase in a signal indicating cell death, is detected after and/or during the incubation. NK-92 cells are commercially available, e.g. from Conkwest; Del Mar, Calif.

Traditionally, monoclonal antibodies have been produced as native molecules in murine hybridoma lines. In addition to that technology, the methods and compositions described herein provide for recombinant DNA expression of monoclonal antibodies. This allows the production of humanized antibodies as well as a spectrum of antibody derivatives and fusion proteins in a host species of choice. The production of antibodies in bacteria, yeast, transgenic animals and chicken eggs are also alternatives for hybridoma-based production systems. The main advantages of transgenic animals are potential high yields from renewable sources.

Nucleic acid molecules encoding amino acid sequence variants of antibodies are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody. A nucleic acid sequence encoding at least one antibody, portion or polypeptide as described herein can be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, e.g., by Maniatis et al., Molecular Cloning, Lab. Manual (Cold Spring Harbor Lab. Press, NY, 1982 and 1989), and Ausubel, 1987, 1993, and can be used to construct nucleic acid sequences which encode a monoclonal antibody molecule or antigen binding region thereof.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression as peptides or antibody portions in recoverable amounts. The precise nature of the regulatory regions needed for gene expression may vary from organism to organism, as is well known in the analogous art. See, e.g., Sambrook et al., 1989; Ausubel et al., 1987-1993.

Accordingly, the expression of an antibody or antigen-binding portion thereof as described herein can occur in either prokaryotic or eukaryotic cells. Suitable hosts include bacterial or eukaryotic hosts, including yeast, insects, fungi, bird and mammalian cells either in vivo, or in situ, or host cells of mammalian, insect, bird or yeast origin. The mammalian cell or tissue can be of human, primate, hamster, rabbit, rodent, cow, pig, sheep, horse, goat, dog or cat origin, but any other mammalian cell may be used. Further, by use of, for example, the yeast ubiquitin hydrolase system, in vivo synthesis of ubiquitin-transmembrane polypeptide fusion proteins can be accomplished. The fusion proteins so produced can be processed in vivo or purified and processed in vitro, allowing synthesis of an antibody or portion thereof as described herein with a specified amino terminus sequence. Moreover, problems associated with retention of initiation codon-derived methionine residues in direct yeast (or bacterial) expression maybe avoided. Sabin et al., 7 Bio/Technol. 705 (1989); Miller et al., 7 Bio/Technol. 698 (1989). Any of a series of yeast gene expression systems incorporating promoter and termination elements from the actively expressed genes coding for glycolytic enzymes produced in large quantities when yeast are grown in mediums rich in glucose can be utilized to obtain recombinant antibodies or antigen-binding portions thereof as described herein. Known glycolytic genes can also provide very efficient transcriptional control signals. For example, the promoter and terminator signals of the phosphoglycerate kinase gene can be utilized.

Production of antibodies or antigen-binding portions thereof as described herein in insects can be achieved. For example, by infecting the insect host with a baculovirus engineered to express a transmembrane polypeptide by methods known to those of skill. See Ausubel et al., 1987, 1993.

In some embodiments, the introduced nucleotide sequence is incorporated into a plasmid or viral vector capable of autonomous replication in the recipient host. Any of a wide variety of vectors can be employed for this purpose and are known and available to those or ordinary skill in the art. See, e.g., Ausubel et al., 1987, 1993. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Example prokaryotic vectors known in the art include plasmids such as those capable of replication in *E. coli.*, for example. Other gene expression elements useful for the expression of cDNA encoding antibodies or antigen-binding portions thereof include, but are not limited to (a) viral transcription promoters and their enhancer elements, such as the SV40 early promoter. (Okayama et al., 3 Mol. Cell. Biol. 280 (1983)), Rous sarcoma virus LTR (Gorman et al., 79 PNAS 6777 (1982)), and Moloney murine leukemia virus LTR (Grosschedl et al., 41 Cell 885 (1985)); (b) splice regions and polyadenylation sites such as those derived from the SV40 late region (Okayarea et al., 1983), and (c) polyadenylation sites such as in SV40 (Okayama et al., 1983). Immunoglobulin cDNA genes can be expressed as described by Liu et al., infra, and Weidle et al., 51 Gene 21 (1987), using as expression elements the SV40 early promoter and its enhancer, the mouse immunoglobulin H chain promoter enhancers, SV40 late region mRNA splicing, rabbit S-globin intervening sequence, immunoglobulin and rabbit S-globin polyadenylation sites, and SV40 polyadenylation elements.

For immunoglobulin genes comprised of part cDNA, part genomic DNA (Whittle et al., 1 Protein Engin. 499 (1987)), the transcriptional promoter can be human cytomegalovirus, the promoter enhancers can be cytomegalovirus and mouse/human immunoglobulin, and mRNA splicing and polyadenylation regions can be the native chromosomal immunoglobulin sequences.

In some embodiments, for expression of cDNA genes in rodent cells, the transcriptional promoter is a viral LTR sequence, the transcriptional promoter enhancers are either or both the mouse immunoglobulin heavy chain enhancer and the viral LTR enhancer, the splice region contains an intron of greater than 31 bp, and the polyadenylation and transcription termination regions are derived from the native chromosomal sequence corresponding to the immunoglobulin chain being synthesized. In other embodiments, cDNA sequences encoding other proteins are combined with the above-recited expression elements to achieve expression of the proteins in mammalian cells.

Each fused gene is assembled in, or inserted into, an expression vector. Recipient cells capable of expressing the chimeric immunoglobulin chain gene product are then transfected singly with an antibody, antigen-binding portion thereof, or chimeric H or chimeric L chain-encoding gene, or are co-transfected with a chimeric H and a chimeric L chain gene. The transfected recipient cells are cultured under conditions that permit expression of the incorporated genes and the expressed immunoglobulin chains or intact antibodies or fragments are recovered from the culture.

In some embodiments, the fused genes encoding the antibody, antigen-binding fragment thereof, or chimeric H and L chains, or portions thereof are assembled in separate expression vectors that are then used to co-transfect a recipient cell. Each vector can contain two selectable genes, a first selectable gene designed for selection in a bacterial system and a second selectable gene designed for selection in a eukaryotic system, wherein each vector has a different pair of genes. This strategy results in vectors which first direct the production, and permit amplification, of the fused genes in a bacterial system. The genes so produced and amplified in a bacterial host are subsequently used to co-transfect a eukaryotic cell, and allow selection of a co-transfected cell carrying the desired transfected genes. Non-limiting examples of selectable genes for use in a bacterial system are the gene that confers resistance to ampicillin and the gene that confers resistance to chloramphenicol. Selectable genes for use in eukaryotic transfectants include the xanthine guanine phosphoribosyl transferase gene (designated gpt) and the phosphotransferase gene from Tn5 (designated neo). Alternatively the fused genes encoding chimeric H and L chains can be assembled on the same expression vector.

For transfection of the expression vectors and production of the chimeric, humanized, or composite human antibodies described herein, the recipient cell line can be a myeloma cell. Myeloma cells can synthesize, assemble and secrete immunoglobulins encoded by transfected immunoglobulin genes and possess the mechanism for glycosylation of the immunoglobulin. For example, in some embodiments, the recipient cell is the recombinant Ig-producing myeloma cell SP2/0 (ATCC #CRL 8287). SP2/0 cells produce only immunoglobulin encoded by the transfected genes. Myeloma cells can be grown in culture or in the peritoneal cavity of a mouse, where secreted immunoglobulin can be obtained from ascites fluid. Other suitable recipient cells include lymphoid cells such as B lymphocytes of human or non-human origin, hybridoma cells of human or non-human origin, or interspecies heterohybridoma cells.

An expression vector carrying a chimeric, humanized, or composite human antibody construct, antibody, or antigen-binding portion thereof as described herein can be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and microprojectile bombardment. Johnston et al., 240 Science 1538 (1988), as known to one of ordinary skill in the art.

Yeast provides certain advantages over bacteria for the production of immunoglobulin H and L chains. Yeasts carry out post-translational peptide modifications including glycosylation. A number of recombinant DNA strategies exist that utilize strong promoter sequences and high copy number plasmids which can be used for production of the desired proteins in yeast. Yeast recognizes leader sequences of cloned mammalian gene products and secretes peptides bearing leader sequences (i.e., pre-peptides). Hitzman et al., 11th Intl. Conf. Yeast, Genetics & Molec. Biol. (Montpelier, France, 1982).

Yeast gene expression systems can be routinely evaluated for the levels of production, secretion and the stability of antibodies, and assembled chimeric, humanized, or composite human antibodies, portions and regions thereof. Any of a series of yeast gene expression systems incorporating promoter and termination elements from the actively expressed genes coding for glycolytic enzymes produced in large quantities when yeasts are grown in media rich in glucose can be utilized. Known glycolytic genes can also provide very efficient transcription control signals. For example, the promoter and terminator signals of the phosphoglycerate kinase (PGK) gene can be utilized. A number of approaches can be taken for evaluating optimal expression plasmids for the expression of cloned immunoglobulin cDNAs in yeast. See II DNA Cloning 45, (Glover, ed., IRL Press, 1985) and e.g., U.S. Publication No. US 2006/0270045 A1.

Bacterial strains can also be utilized as hosts for the production of the antibody molecules or peptides described herein, *E. coli* K12 strains such as *E. coli* W3110 (ATCC 27325), *Bacillus* species, enterobacteria such as *Salmonella typhimurium* or *Serratia marcescens*, and various *Pseudomonas* species can be used. Plasmid vectors containing replicon and control sequences which are derived from species compatible with a host cell are used in connection with these bacterial hosts. The vector carries a replication site, as well as specific genes which are capable of providing phenotypic selection in transformed cells. A number of approaches can be taken for evaluating the expression plasmids for the production of chimeric, humanized, or composite humanized antibodies and fragments thereof encoded by the cloned immunoglobulin cDNAs or CDRs in bacteria (see Glover, 1985; Ausubel, 1987, 1993; Sambrook, 1989; Colligan, 1992-1996).

Host mammalian cells can be grown in vitro or in vivo. Mammalian cells provide post-translational modifications to immunoglobulin protein molecules including leader peptide removal, folding and assembly of H and L chains, glycosylation of the antibody molecules, and secretion of functional antibody protein.

Mammalian cells which can be useful as hosts for the production of antibody proteins, in addition to the cells of lymphoid origin described above, include cells of fibroblast origin, such as Vero (ATCC CRL 81) or CHO-K1 (ATCC CRL 61) cells. Exemplary eukaryotic cells that can be used to express polypeptides include, but are not limited to, COS cells, including COS 7 cells; 293 cells, including 293-6E cells; CHO cells, including CHO—S and DG44 cells; PER.C6™ cells (Crucell); and NS0 cells. In some embodiments, a particular eukaryotic host cell is selected based on its ability to make desired post-translational modifications to the heavy chains and/or light chains. For example, in some embodiments, CHO cells produce polypeptides that have a higher level of sialylation than the same polypeptide produced in 293 cells.

In some embodiments, one or more antibodies or antigen-binding portions thereof as described herein can be produced in vivo in an animal that has been engineered or transfected with one or more nucleic acid molecules encoding the polypeptides, according to any suitable method.

In some embodiments, an antibody or antigen-binding portion thereof as described herein is produced in a cell-free system. Nonlimiting exemplary cell-free systems are described, e.g., in Sitaraman et al., Methods Mol. Biol. 498: 229-44 (2009); Spirin, Trends Biotechnol. 22: 538-45 (2004); Endo et al., Biotechnol. Adv. 21: 695-713 (2003).

Many vector systems are available for the expression of cloned H and L chain genes in mammalian cells (see Glover, 1985). Different approaches can be followed to obtain complete $H_2L_2$ antibodies. As discussed above, it is possible to co-express H and L chains in the same cells to achieve intracellular association and linkage of H and L chains into complete tetrameric $H_2L_2$ antibodies or antigen-binding portions thereof. The co-expression can occur by using either the same or different plasmids in the same host. Genes for both H and L chains or portions thereof can be placed into the same plasmid, which is then transfected into cells, thereby selecting directly for cells that express both chains. Alternatively, cells can be transfected first with a plasmid encoding one chain, for example the L chain, followed by transfection of the resulting cell line with an H chain plasmid containing a second selectable marker. Cell lines producing antibodies, antigen-binding portions thereof and/or $H_2L_2$ molecules via either route could be transfected with plasmids encoding additional copies of peptides, H, L, or H plus L chains in conjunction with additional selectable markers to generate cell lines with enhanced properties, such as higher production of assembled $H_2L_2$ antibody molecules or enhanced stability of the transfected cell lines.

Additionally, plants have emerged as a convenient, safe and economical alternative main-stream expression systems for recombinant antibody production, which are based on large scale culture of microbes or animal cells. Antibodies can be expressed in plant cell culture, or plants grown conventionally. The expression in plants may be systemic, limited to susb-cellular plastids, or limited to seeds (endosperms). See, e.g., U.S. Patent Pub. No. 2003/0167531; U.S. Pat. No. 6,080, 560; No. 6,512,162; WO 0129242. Several plant-derived antibodies have reached advanced stages of development, including clinical trials (see, e.g., Biolex, NC).

In some aspects, provided herein are methods and systems for the production of a humanized antibody, which is prepared by a process which comprises maintaining a host transformed with a first expression vector which encodes the light chain of the humanized antibody and with a second expression vector which encodes the heavy chain of the humanized antibody under such conditions that each chain is expressed and isolating the humanized antibody formed by assembly of the thus-expressed chains. The first and second expression vectors can be the same vector. Also provided herein are DNA sequences encoding the light chain or the heavy chain of the humanized antibody; an expression vector which incorporates a said DNA sequence; and a host transformed with a said expression vector.

Generating a humanized antibody from the sequences and information provided herein can be practiced by those of ordinary skill in the art without undue experimentation. In one approach, there are four general steps employed to humanize a monoclonal antibody, see, e.g., U.S. Pat. No. 5,585,089; No. 6,835,823; No. 6,824,989. These are: (1) determining the nucleotide and predicted amino acid sequence of the starting antibody light and heavy variable domains; (2) designing the humanized antibody, i.e., deciding which antibody framework region to use during the humanizing process; (3) the actual humanizing methodologies/techniques; and (4) the transfection and expression of the humanized antibody.

Usually the CDR regions in humanized antibodies and human antibody variants are substantially identical, and more usually, identical to the corresponding CDR regions in the mouse or human antibody from which they were derived. Although not usually desirable, it is sometimes possible to make one or more conservative amino acid substitutions of CDR residues without appreciably affecting the binding affinity of the resulting humanized immunoglobulin or human antibody variant. Occasionally, substitutions of CDR regions can enhance binding affinity.

In addition, techniques developed for the production of "chimeric antibodies" (see Morrison et al., Proc. Natl. Acad. Sci. 81:851-855 (1984); Neuberger et al., Nature 312:604-608 (1984); Takeda et al., Nature 314:452-454 (1985); which are incorporated by reference herein in their entireties) by splicing genes from a mouse, or other species, antibody molecule of appropriate antigen specificity together with genes from a human antibody molecule of appropriate biological activity can be used. A chimeric antibody is a molecule in which different portions are derived from different animal species, such as those having a variable region derived from a murine monoclonal antibody and a human immunoglobulin constant region, e.g., humanized antibodies.

The variable segments of chimeric antibodies are typically linked to at least a portion of an immunoglobulin constant region (Fc), typically that of a human immunoglobulin. Human constant region DNA sequences can be isolated in accordance with well-known procedures from a variety of human cells, such as immortalized B-cells (WO 87/02671; which is incorporated by reference herein in its entirety). The antibody can contain both light chain and heavy chain constant regions. The heavy chain constant region can include CH1, hinge, CH2, CH3, and, sometimes, CH4 regions. For therapeutic purposes, the CH2 domain can be deleted or omitted.

Alternatively, techniques described for the production of single chain antibodies (see, e.g. U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989); which are incorporated by reference herein in their entireties) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* can also be used (see, e.g. Skerra et al., Science 242:1038-1041 (1988); which is incorporated by reference herein in its entirety).

Chimeric, humanized and human antibodies are typically produced by recombinant expression. Recombinant polynucleotide constructs typically include an expression control sequence operably linked to the coding sequences of antibody chains, including naturally-associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the cross-reacting antibodies. These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences. *E. coli* is one prokaryotic host particularly useful for cloning the DNA sequences. Microbes, such as yeast are also useful for expression. *Saccharomyces* is a preferred yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization. Mammalian cells are a preferred host for expressing nucleotide segments encoding immunoglobulins or fragments thereof. See Winnacker, From Genes to Clones, (VCH Publishers, NY, 1987), which is incorporated herein by reference in its entirety. A number of suitable host cell lines capable of secreting intact heterologous proteins have been developed in the art, and include CHO cell lines, various COS cell lines, HeLa cells, L cells and multiple myeloma cell lines. Expression vectors for these cells can include expression control sequences, such as an origin of replication, a promoter, an enhancer (Queen et al., "Cell-type Specific Regulation of a Kappa Immunoglobulin Gene by Promoter and Enhancer Elements," *Immunol Rev* 89:49 (1986), incorporated herein by reference in its entirety), and necessary processing information sites, such as ribosome binding sites, RNA splice sites, polyadenylation sites, and transcriptional terminator sequences. Preferred expression control sequences are promoters substantially similar to a region of the endogenous genes, cytomegalovirus, SV40, adenovirus, bovine papillomavirus, and the like. See Co et al., "Chimeric and Humanized Antibodies with Specificity for the CD33 Antigen," *J Immunol* 148:1149 (1992), which is incorporated herein by reference in its entirety. Alternatively, antibody coding sequences can be incorporated in transgenes for introduction into the genome of a transgenic animal and subsequent expression in the milk of the transgenic animal (e.g., according to methods described in U.S. Pat. Nos. 5,741,957, 5,304,489, 5,849,992, all incorporated by reference herein in their entireties). Suitable transgenes include coding sequences for light and/or heavy chains in operable linkage with a promoter and enhancer from a mammary gland specific gene, such as casein or beta lactoglobulin. The vectors containing the DNA segments of interest can be transferred into the host cell by well-known methods, depending on the type of cellular host. For example, calcium chloride transfection is commonly utilized for prokaryotic cells, whereas calcium phosphate treatment, electroporation, lipofection, biolistics or viral-based transfection can be used for other cellular hosts. Other methods used to transform mammalian cells include the use of polybrene, protoplast fusion, liposomes, electroporation, and microinjection (see generally, Sambrook et al., supra, which is herein incorporated by reference in is entirety). For production of transgenic animals, transgenes can be microinjected into fertilized oocytes, or can be incorporated into the genome of embryonic stem cells, and the nuclei of such cells transferred into enucleated oocytes. Once expressed, antibodies can be purified according to standard procedures of the art, including HPLC purification, column chromatography, gel electrophoresis and the like (see generally, Scopes, Protein Purification (Springer-Verlag, NY, 1982), which is incorporated herein by reference in its entirety).

Once expressed, the whole antibodies, their dimers, individual light and heavy chains, or other immunoglobulin forms of the present invention can be recovered and purified by known techniques, e.g., immunoabsorption or immunoaffinity chromatography, chromatographic methods such as HPLC (high performance liquid chromatography), ammonium sulfate precipitation, gel electrophoresis, or any combination of these. See generally, Scopes, PROTEIN PURIF. (Springer-Verlag, NY, 1982). Substantially pure immunoglobulins of at least about 90% to 95% homogeneity are advantageous, as are those with 98% to 99% or more homogeneity, particularly for pharmaceutical uses. Once purified, partially or to homogeneity as desired, a humanized or composite human antibody can then be used therapeutically or in developing and performing assay procedures, immunofluorescent stainings, and the like. See generally, Vols. I & II Immunol. Meth. (Lefkovits & Pernis, eds., Acad. Press, NY, 1979 and 1981).

Additionally, and as described herein, a recombinant humanized antibody can be further optimized to decrease potential immunogenicity, while maintaining functional activity, for therapy in humans. In this regard, functional activity means a polypeptide capable of displaying one or more known functional activities associated with a recombinant antibody or antigen-binding portion thereof as described herein. Such functional activities include reduction of MIC shedding and/or the ability to bind to the epitope comprising the amino acid sequence of SEQ ID NO: 1. Additionally, a polypeptide having functional activity means the polypeptide exhibits activity similar, but not necessarily identical to, an activity of a reference antibody or antigen-binding portion thereof as described herein, including mature forms, as measured in a particular assay, such as, for example, a biological assay, with or without dose dependency. In the case where dose dependency does exist, it need not be identical to that of the reference antibody or antigen-binding portion thereof, but rather substantially similar to the dose-dependence in a given activity as compared to the reference antibody or antigen-binding portion thereof as described herein (i.e., the candidate polypeptide will exhibit greater activity, or not more than about 25-fold less, about 10-fold less, or about 3-fold less activity relative to the antibodies and antigen-binding fragments described herein, such as the polypeptide of SEQ ID NO:8).

The activity of an antibody or an antigen-binding portion thereof, for example, the inhibitory effect of the antibodies on MIC shedding can be determined. Such methods are described above herein.

In some embodiments, the technology described herein relates to a nucleic acid encoding an antibody or antigen-binding portion thereof as described herein. As used herein, the term "nucleic acid" or "nucleic acid sequence" refers to a polymeric molecule incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA.

In some embodiments, a nucleic acid encoding an antibody or antigen-binding portion thereof as described herein is comprised by a vector. In some of the aspects described herein, a nucleic acid sequence encoding an antibody or antigen-binding portion thereof as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain the nucleic acid encoding an antibody or antigen-binding portion thereof as described herein in place of non-essential viral genes. The vector and/or particle may be utilized for the purpose of transferring any nucleic acids into cells either in vitro or in vivo. Numerous forms of viral vectors are known in the art.

By "recombinant vector" is meant a vector that includes a heterologous nucleic acid sequence, or "transgene" that is capable of expression in vivo. It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

Aspects of the technology described herein relate to compositions comprising an antibody or antigen-binding portion thereof as described herein or a nucleic acid encoding an antibody or antigen-binding portion thereof as described herein. In some embodiments, the composition is a pharmaceutical composition. As used herein, the term "pharmaceutical composition" refers to the active agent in combination with a pharmaceutically acceptable carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance or maintain the effectiveness of the active ingredient. The therapeutic composition as described herein can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the invention that will be effective in the treatment of a particular disorder or condition will depend on the nature of the disorder or condition, and can be determined by standard clinical techniques.

In some embodiments, the composition comprising an antibody or antigen-binding portion thereof as described herein or a nucleic acid encoding an antibody or antigen-binding portion thereof as described herein can be a lyophilisate.

In some embodiments, the technology described herein relates to a syringe comprising a therapeutically effective amount of a composition described herein.

As used herein, the phrase "therapeutically effective amount", "effective amount" or "effective dose" refers to an amount that provides a therapeutic or aesthetic benefit in the treatment, prevention, or management of a tumor or malginancy, e.g. an amount that provides a statistically significant decrease in at least one symptom, sign, or marker of a tumor or malignancy. Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

In one aspect, the technology described herein relates to a method of inhibiting MIC shedding by a cell, the method comprising contacting the cell with an antibody or antigen-binding portion thereof as described herein. In some embodiments, the cell can be ex vivo. In some embodiments, the cell can be in vivo. In some embodiments, the cell can be an epithelial tumor cell or a cell of a hematopoietic malignancy.

In one aspect, the technology described herein relates to a method comprising administering an antibody or antigen-binding portion thereof as described herein or a nucleic acid encoding an antibody or antigen-binding portion thereof as described herein to a subject. In some embodiments, the subject is in need of treatment for an epithelial cell tumor or a hematopoietic malignancy. In some embodiments, the method is a method of treating a subject. In some embodiments, the method is a method of treating an epithelial cell tumor or a hematopoietic malignancy in a subject.

A "cancer", "malignancy", or "tumor" as used herein refers to an uncontrolled growth of cells which interferes with the normal functioning of the bodily organs and systems. A subject that has a cancer or a tumor is a subject having objectively measurable cancer cells present in the subject's body. Included in this definition are benign tumors and malignant cancers, as well as potentially dormant tumors or micrometastatses. Cancers which migrate from their original location and seed other vital organs can eventually lead to the death of the subject through the functional deterioration of the affected organs. Hemopoietic cancers, such as leukemia, are able to out-compete the normal hemopoietic compartments in a subject, thereby leading to hemopoietic failure (in the form of anemia, thrombocytopenia and neutropenia) ultimately causing death.

Examples of cancer include but are not limited to, carcinoma, lymphoma, blastoma, sarcoma, and leukemia. More particular examples of such cancers include, but are not limited to, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma (GBM); hepatic carcinoma; hepatoma; intra-epithelial neoplasm.; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx);

ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

In some embodiments, the tumor or malignancy is MIC-positive. As used herein, the term "MIC-positive tumor" is used to describe a tumor cell, a cluster of tumor cells or a tumor mass, which produces a MIC protein. This term is intended to encompass all tumor cells and/or tumor masses that shed all or part of a MIC protein, thus these cells may only display a MIC protein on its surface for a short time period—that is, the term encompasses tumors that shed MIC protein, regardless of whether detectable MIC protein remains present on their cell surface or not. However, any tumor that is capable of escaping innate immune rejection by shedding MIC is considered to be a "MIC-positive tumor" as that term is used herein. Some non-limiting examples of MIC-positive tumors include epithelial cell tumors and hematopoietic malignancies.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient", "individual" and "subject" are used interchangeably herein.

Preferably, the subject is a mammal. The mammal can be a human, non-human primate, mouse, rat, dog, cat, horse, or cow, but are not limited to these examples. Mammals other than humans can be advantageously used, for example, as subjects that represent animal models of, for example, various cancers. In addition, the methods described herein can be used to treat domesticated animals and/or pets. A subject can be male or female.

A subject can be one who has been previously diagnosed with or identified as suffering from or having a condition in need of treatment (e.g. a tumor) or one or more complications related to such a condition, and optionally, but need not have already undergone treatment for a condition or the one or more complications related to the condition. Alternatively, a subject can also be one who has not been previously diagnosed as having a condition in need of treatment or one or more complications related to such a condition. For example, a subject can be one who exhibits one or more risk factors for a condition or one or more complications related to a condition or a subject who does not exhibit risk factors. A "subject in need" of treatment for a particular condition can be a subject having that condition, diagnosed as having that condition, or at risk of developing that condition.

As used herein, the terms "treat," "treatment," "treating," or "amelioration" when used in reference to a disease, disorder or medical condition, refer to therapeutic treatments for a condition, wherein the object is to reverse, alleviate, ameliorate, inhibit, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a condition is reduced or halted. That is, "treatment" includes not just the improvement of symptoms or markers, but also a cessation or at least slowing of progress or worsening of symptoms that would be expected in the absence of treatment. Beneficial or desired clinical results include, but are not limited to, alleviation of one or more symptom(s), diminishment of extent of the deficit, stabilized (i.e., not worsening) state of a tumor or malignancy, delay or slowing of tumor growth and/or metastasis, and an increased lifespan as compared to that expected in the absence of treatment. As used herein, the term "administering," refers to the placement of an antibody or antigen-binding portion thereof as described herein or a nucleic acid encoding an antibody or antigen-binding portion thereof as described herein into a subject by a method or route which results in at least partial localization of the agents at a desired site. The pharmaceutical composition comprising an antibody or antigen-binding portion thereof as described herein or a nucleic acid encoding an antibody or antigen-binding portion thereof as described herein disclosed herein can be administered by any appropriate route which results in an effective treatment in the subject.

The dosage ranges for the agent depend upon the potency, and encompass amounts large enough to produce the desired effect e.g., slowing of tumor growth or a reduction in tumor size. The dosage should not be so large as to cause unacceptable adverse side effects. Generally, the dosage will vary with the age, condition, and sex of the patient and can be determined by one of skill in the art. The dosage can also be adjusted by the individual physician in the event of any complication. In some embodiments, the dosage ranges from 0.001 mg/kg body weight to 0.5 mg/kg body weight. In some embodiments, the dose range is from 5 µg/kg body weight to 100 µg/kg body weight. Alternatively, the dose range can be titrated to maintain serum levels between 1 µg/mL and 1000 µg/mL.

Administration of the doses recited above can be repeated. In fact, to the extent that inhibition of MIC shedding can promote immune attack on a tumor, long term administration is contemplated, e.g. first to treat the tumor itself, and then to provide continued surveillance against the development of tumor cells that gain the ability to shed MIC. In some embodiments, the doses are given once a day, or multiple times a day, for example but not limited to three times a day. In a preferred embodiment, the doses recited above are administered daily for several weeks or months. The duration of treatment depends upon the subject's clinical progress and responsiveness to therapy.

A therapeutically effective amount is an amount of an agent that is sufficient to produce a statistically significant, measurable change in tumor size, tumor growth etc. (efficacy measurements are described below herein). Such effective amounts can be gauged in clinical trials as well as animal studies.

An agent can be administered intravenously by injection or by gradual infusion over time. Given an appropriate formulation for a given route, for example, agents useful in the methods and compositions described herein can be administered intravenously, intranasally, by inhalation, intraperitoneally, intramuscularly, subcutaneously, intracavity, and can be delivered by peristaltic means, if desired, or by other means known by those skilled in the art. It is preferred that the compounds used herein are administered orally, intravenously or intramuscularly to a patient having cancer. Local administration directly to a tumor mass is also specifically contemplated.

Therapeutic compositions containing at least one agent can be conventionally administered in a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired.

Precise amounts of active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

In some embodiments, the methods further comprise administering the pharmaceutical composition described herein along with one or more additional chemotherapeutic agents, biologics, drugs, or treatments as part of a combinatorial therapy. In some such embodiments, the chemotherapeutic agent biologic, drug, or treatment is selected from the group consisting of: radiation therapy, surgery, gemcitabine, cisplastin, paclitaxel, carboplatin, bortezomib, AMG479, vorinostat, rituximab, temozolomide, rapamycin, ABT-737, and PI-103.

In some embodiments of the methods described herein, the methods further comprise administering one or more chemotherapeutic agentd to the subject being administered the pharmaceutical composition described herein. Non-limiting examples of chemotherapeutic agents can include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKCalpha, Raf, H-Ras, EGFR (e.g., erlotinib (Tarceva®)) and VEGF-A that reduce cell proliferation and pharmaceutically acceptable salts, acids or derivatives of any of the above.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins, such as small molecule toxins or enzymatically active toxins of bacterial, fungal, plant or animal origin, including fragments and/or variants thereof.

As used herein, the terms "chemotherapy" or "chemotherapeutic agent" refer to any chemical agent with therapeutic usefulness in the treatment of diseases characterized by abnormal cell growth. Such diseases include tumors, neoplasms and cancer as well as diseases characterized by hyperplastic growth. Chemotherapeutic agents as used herein encompass both chemical and biological agents. These agents function to inhibit a cellular activity upon which the cancer cell depends for continued survival. Categories of chemotherapeutic agents include alkylating/alkaloid agents, antimetabolites, hormones or hormone analogs, and miscellaneous antineoplastic drugs. Most if not all of these agents are directly toxic to cancer cells and do not require immune stimulation. In one embodiment, a chemotherapeutic agent is an agent of use in treating neoplasms such as solid tumors. In one embodiment, a chemotherapeutic agent is a radioactive molecule. One of skill in the art can readily identify a chemotherapeutic agent of use (e.g. see Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology $2^{nd}$ Edition, 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). The bispecific and multispecific polypeptide agents described herein can be used in conjunction with additional chemotherapeutic agents.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one time administration and typical dosages range from 10 to 200 units (Grays) per day.

The efficacy of a given treatment for cancer can be determined by the skilled clinician. However, a treatment is considered "effective treatment," as the term is used herein, if any one or all of the signs or symptoms of e.g., a tumor are altered in a beneficial manner or other clinically accepted symptoms are improved, or even ameliorated, e.g., by at least 10% following treatment with an agent as described herein. Efficacy can also be measured by a failure of an individual to worsen as assessed by hospitalization or need for medical interventions (i.e., progression of the disease is halted). Methods of measuring these indicators are known to those of skill in the art and/or described herein.

An effective amount for the treatment of a disease means that amount which, when administered to a mammal in need thereof, is sufficient to result in effective treatment as that term is defined herein, for that disease. Efficacy of an agent can be determined by assessing physical indicators of, for example cancer, e.g., tumor size, tumor mass, tumor density, angiogenesis, tumor growth rate, etc. In addition, efficacy of an agent can be measured by a decrease in circulating MIC peptides or fragments thereof in a subject being treated with an agent comprising an antibody or antigen-binding portion thereof as described herein or a nucleic acid encoding an antibody or antigen-binding portion thereof as described herein.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

This invention is further illustrated by the following examples which should not be construed as limiting.

EXAMPLE

Example 1

Methods for Treating Cancer by Inhibiting MIC Shedding

Whether NKG2D ligand expression contributes to immune protection or suppression during tumor development remains paradoxical. Described herein are novel lines of transgenic mice that specifically express the shedding-sensitive NKG2D ligand MICB or the shedding-resistant membrane-restricted NKG2D ligand MICB.A2 in the prostate. After crossing with the TRAMP model of spontaneous prostate carcinogenesis, bi-transgenic TRAMP-MICB mice showed a significantly higher incidence of poorly-differentiated carcinomas and associated metastasis in contrast to TRAMP-MICB.A2 mice that remained tumor-free survival. Tumor suppression was owing to sustained MICB.A2-induced NKG2D-mediated NK and CD8 T cell immunity while the tumor-derived soluble MICB in TRAMP-MICB mice conferred immune suppression and facilitated tumor progression. These data support strategies to stabilize tumor-specific expression of NKG2D ligands as viable avenues for translational research. The genesis and progression of prostate cancer in an autochthonous genetically engineered mouse model is facilitated by expression of tumor-associated soluble NKG2D ligand while inhibited by a non-soluble membrane-restricted form.

NKG2D is a C-type lectin-like surface receptor expressed by all nature killer (NK) cells, most NKT cells, subsets of γδT cells, all human CD8 T cells and activated mouse CD8 T cells[1, 2]. Engagement of NKG2D by ligand in vitro can activate NK cells and co-stimulate CD8 and γδT cells[3-7]. In humans, known ligands for NKG2D include the major histocompatibility complex (MHC) class I chain-related molecules (MIC) family members MICA and MICB8 and a family of UL-16 binding proteins (ULBPs) 1-5[9, 10]. In murine systems, the known ligands for NKG2D include the retinoic acid early inducible family of proteins RAE-1[11,12], the minor histocompatibility antigen H60 and its variants[11], as well as the murine ULBP-like transcript 1 (MULT1)[13, 14]. No homolog of human MIC has yet been described in mice although the mouse NKG2D can recognize human MICB and selective alleles of human MICA[15-18].

NKG2D function has been implicated to be of significance in tumor immunity in experimental animal models[11, 12, 19, 20]. Enforced expression of NKG2D ligand RAE-1 or H60 causes tumor cells to be rejected in syngeneic mice in a manner dependent on NK cells and, in some cases, primed CD8 T cells[11,12]. NKG2D neutralization in vivo with a specific antibody enhances host sensitivity to carcinogen-induced spontaneous tumor initiation[20]. More recently, the genetically engineered prostate cancer prone TRAMP (transgenic adenocarcinoma of the mouse prostate) mice were shown three times more likely to have aggressive poorly-differentiated prostate tumors when NKG2D-deficient than their wild type counterparts[19].

It is evident that NKG2D-mediated tumor immunity becomes subverted in cancer patients. Curiously, most clinical tumors, in particular those of epithelial origin, express abundant NKG2D ligands MIC 1,[8, 21, 22] and yet progress to advanced disease. One of the mechanisms proposed to explain how human tumors progress and evade NKG2D immune surveillance was through the shedding of membrane-bound MIC to yield a soluble sMIC form that has been shown to negatively-regulate NKG2D function[21]. Indeed, clinical data showing that elevated serum levels of sMIC correlate with advanced epithelial malignancies tends to support this hypothesis[22-29]. However, an alternative hypothesis based on studies with constitutive expression of NKG2D ligands in normal mouse suggests that chronic exposure to membrane-bound NKG2D ligands can also impair NKG2D tumor immunity and allow tumors to progress[30-32]. Unfortunately, these findings support alternative and contradictory roles for NKG2D ligand in tumor immunity.

In an attempt to resolve the apparent paradox, the ability of human MICB to be recognized by mouse NKG2D[16, 17] was exploited and two unique yet independent bi-transgenic mouse models TRAMP-MICB and the TRAMP-MICB.A2 were generated; the former expresses the shedding-sensitive native MICB whilst the latter expresses a shedding-resistant membrane-restricted mutated MICB.A2[16]. In both models, expression of NKG2D ligand M1CB or MICB.A2 is prostate-specific directed by the probasin promoter and concurrent with prostate transformation in the context of the inbred C57BL/6 TRAMP model, closely emulating human cancers. Using these models it was possible to mechanistically address the role of NKG2D ligand expression on NKG2D-dependent tumor immunity.

Results

Generation of transgenic mice expressing a native shedding-sensitive MICB or the shedding-resistant membrane-bound mutated MICB.A2 in prostate epithelium. The inventors have previously described how overexpression of a shedding-resistant membrane-restricted mutated form of MICB (MICB.A2) prevented growth of a C57BL/6 syngeneic TRAMP-C2 xenograft and that MICB.A2-NKG2D mediated in vivo tumor immunity was abrogated by recombinant sMICB, supporting differential roles for soluble MIC and membrane-bound MIC on NKG2D-dependent tumor immunity[16]. The consequence of soluble MIC and membrane-restricted MIC on spontaneous tumor initiation and progression in an immune competent host was further explored as described herein. To this end the shedding-sensitive native MICB and the shedding-resistant membrane-restricted mutant MICB.A2 were targeted to the prostate epithelium of transgenic mice since MICB and MICB.A2 can both be recognized by mouse NKG2D[16]. The resulting transgenic lines could then be crossed to the TRAMP model, in which NKG2D function has been shown to significantly impact tumor development[19].

Figure 1B:
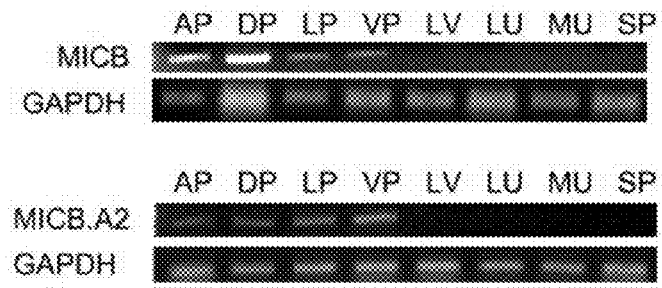

The minimal rat Probasin (rPb) promoter[33] was used to direct expression of MICB and MICB.A2 encoding transgenes to the prostate epithelium in independent lines of C57BL/6 mice (designated as MICB-B6 and MICB.A2-B6 respectively) (FIG. 1A). Integration of a single copy of an intact MICB or MICB.A2 transgene was confirmed in these lines by genomic PCR against a limited template dilution standard (data not shown). RT-PCR demonstrated that MICB and MICB.A2 were expressed specifically by the dorsal, lateral, ventral and anterior prostate lobes but not by other tissues (FIG. 1B). The prostate glands of MICB-B6 and MICB.A2-B6 male mice exhibited normal architecture with stromal structure and intact basal cell layers demonstrated by p63 staining (data not shown). H&E and basal cell cytokeratin p63 staining demonstrated normal structure of the prostates that expressing MICB or MICB.A2. Noticeably, expression of MICB or MICB.A2 in the normal prostates did not seem to instigate an active local immune response as the degree of lymphocyte infiltration determined by CD45 staining in both lines was similar to that observed for wild type C57BL/6 mice (data not shown).

Figure 2:
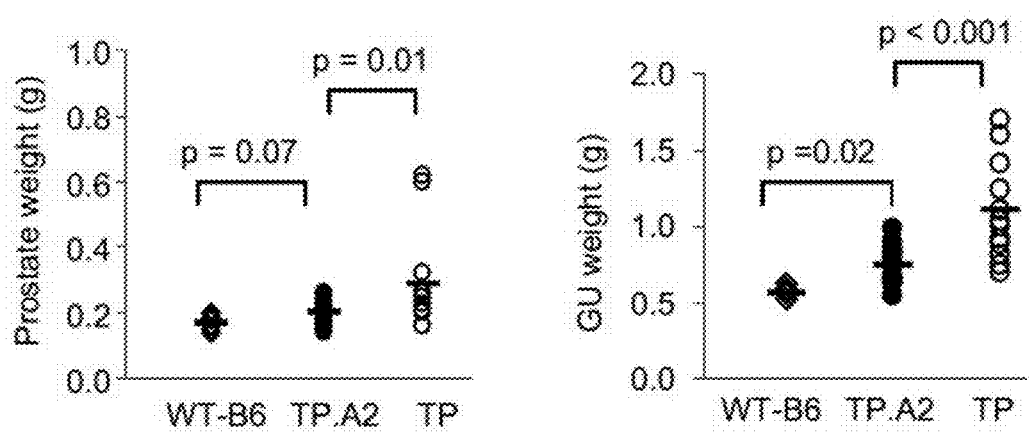
FIG. 2 demonstrates that expression of MICB.A2 in the prostate prevents autochthonous prostate tumorigeneisis in TRAMP mice. Comparison of the prostate and GU weights of TRAMP-MICB.A2 mice (n=14) to TRAMP (n=13) and wild-type B6 (n=10) littermates.

Expression of Shedding-Resistant Membrane-Restricted MICB.A2 Prevents Prostate Tumor Formation. To investigate the impact of expression of membrane-bound NKG2D ligand MIC on prostate tumor development, male MICB.A2 mice were crossed to female TRAMP mice to generate the double transgenic TRAMP-MICB.A2 mice. Normally TRAMP male mice in pure B6 background would develop severe hyperplasia and adenocarcinomas by 18 weeks of age[34, 35]. Remarkably, TRAMP-MICB.A2 mice remained tumor-free as a consequence of rPB-directed expression of MICB.A2 in the prostate epithelium, (FIG. 2). When examined at 24 weeks of age, prostate weights of TRAMP-MICB.A2 mice (0.20±0.01 g; mean±SEM; n=14) were only slightly higher than wild type B6 mice (0.17±0.01 g; n=10) but significantly lower than aged-matched TRAMP mice (0.30±0.04 g; p<0.01, FIG. 2). A wide-range of the genitourinary (GU) weights of the TRAMP-MICB.A2 mice (from 0.62 g to 0.98 g) was observed but remained significantly lower than aged-matched TRAMP mice (p<0.01, FIG. 2). The broader range of GU weights in the TRAMP-MICB.A2 mice in comparison to wild type B6 mice may be attributed to multiple factors, e.g., elevated infiltration of lymphocytes in the prostates (data not shown) and occasionally inflated but benign seminal vesicles (data not shown). It is, however, most important to note that prostate glands from the TRAMP-MICB.A2 mice displayed no histological evidence of carcinoma and that their basal cell layers remained mostly intact as shown by p63 immunostaining (data not shown). H&E and IHC stainings for p63 demonstrated benign prostate histology of TRAMP-MICB.A2 mice.

In comparison, prostate glands from age-matched TRAMP mice showed complete loss of the basal cells consistent with invasive carcinoma (data not shown). Among the 14 TRAMP-MICB.A2 mice examined, four exhibited normal prostate histology determined by p63-immunostaining (data not shown). Prostate glands from 10 of these animals uniformly exhibited varying degree of prostate intraepithelial neoplasia (PIN)-like lesions represented by reduced p63-positivity in the interior of the multilayered lesions and an increased ratio of luminal cell to p63-positive basal cells. Importantly, SV40T antigen was expressed in epithelium of the prostates from all TRAMP-MICB.A2 mice demonstrating expression of the MICB.A2 did not appear to influence expression of the oncogenic-driver transgene. Data also demonstrated that the oncogene SV40T remains to be expressed in these benign prostate epithelium. A significant CD45+ lymphocyte infiltration was noted in these prostate glands in comparison to wild type or B6-MICB.A2 mice (data not shown), suggesting a potential active immunity induced by expression of MICB.A2 on the transformed cells. CD45 immunostaining of the prostate sections demonstrated no or minimal infiltration of CD45+ leukocytes in prostates of the wild type B6 mice, whereas an increased infiltration of CD45+ leukocytes was seen in the prostates of TRAMP and TRAMP-MICB.A2 mice. However, infiltration of CD45+ leukocytes to the prostate of TRAMP mice was mainly restricted to the stromal compartment whereas infiltration CD45+ leukocytes to the prostate of TRAMP-MICB mice was mainly within the gland and associated with the epithelium.

MICB.A2 Sustains NKG2D-Mediated NK Cell and CD8 T Cell Protective Immunity

Figure 3A:
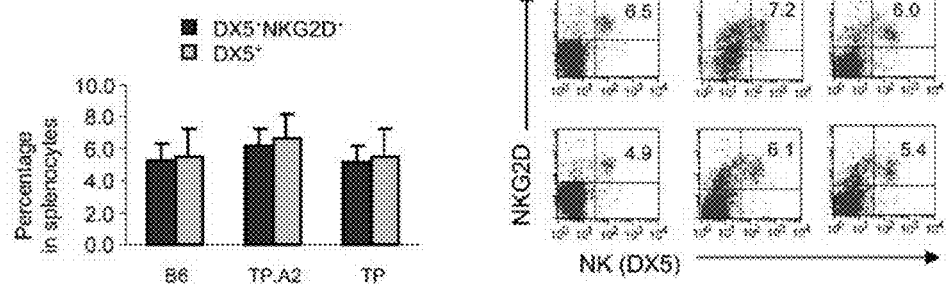
FIGS. 3A-3D demonstrate that shedding-resistant membrane-restricted MICB.A2 sustains NKG2D anti-tumor immunity.
Figure 3B:
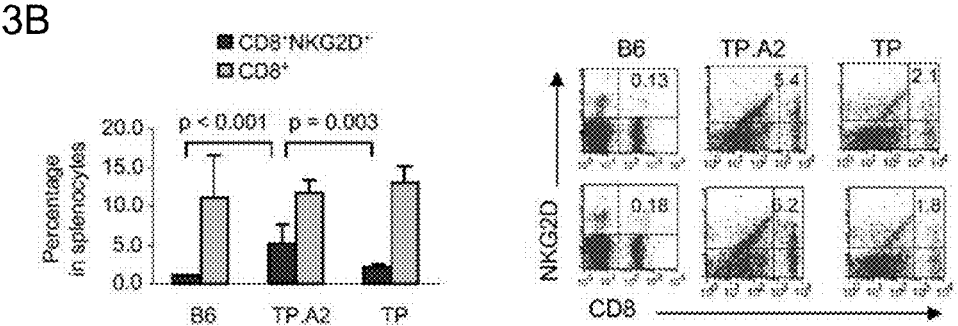
Figure 3C:
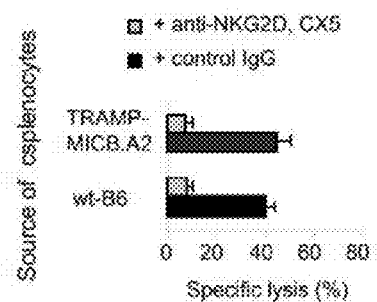

NKG2D expression was next examined in splenic NK and CD8 T cells from TRAMP -MICB.A2 mice. Splenic NK cells from TRAMP-MICB.A2 mice retained comparable levels of NKG2D expression and NKG2D-dependent cytotoxic activity to wild type B6 animals (FIGS. 3A and 3C). Interestingly, TRAMP-MICB.A2 mice demonstrated a trend of elevated population of splenic DX5+ NK cells (FIG. 3A), although not statistically significant. Very remarkably, a significantly elevated population of splenic NKG2D+ CD8 T cells was observed in TRAMP-MICB.A2 mice in comparison to the base level of NKG2D+ CD8 T cells in wild type B6 animals (FIG. 3B). As NKG2D only expressed by activated mouse CD8 T cells[40], these observations indicate an active CD8 T cell immunity in TRAMP-MICB.A2 mice. These data provided direct in vivo evidence that sustained expression of membrane-bound ligand MIC does not impair, but rather stimulates host NKG2D immunity to prevent tumorigenesis.

Figure 3D:
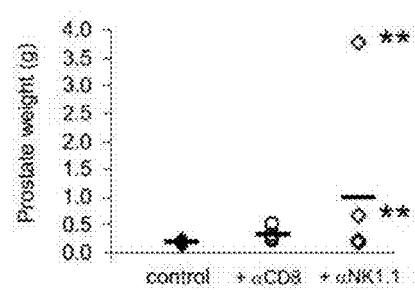

To determine whether both NKG2D-mediated NK cell and T cell immunity are required to prevent tumor initiation, NK1.1 cells or CD8 T cells were depleted from cohorts of 16 to 18-week-old male TRAMP-MICB.A2 mice using anti-NK1.1 (mAb PK136) or anti -CD8 (clone 2.43) for an 8-week period. Depletion of either NK cell or CD8 T cell resulted in a significant increase in prostate wet weights in TRAMP-MICB.A2 mice in comparison to age-matched control mice (FIG. 3D). Depletion of NK cells resulted in development of various grade of carcinomas (WD, MD, and PD). Depletion of CD8 T cells only resulted in development of WD carcinomas. Pathological examination revealed that all the TRAMP-MICB.A2 mice in the treatment group developed carcinoma of the prostate (data not shown). Furthermore, 40% (2/5) of the mice developed PD carcinomas and 40% (2/5) of mice developed MD carcinomas with the depletion of NK cells whereas only WD carcinomas were noted at the time of sacrifice in mice (n=5) depleted for CD8 T cells. These data not only suggest that NKG2D-mediated NK cell and CD8 T cell protection were both required for preventing early tumorigenesis, but that NKG2D-mediated NK cell function may play a more crucial undescribed role in preventing progression.

Figure 4A:
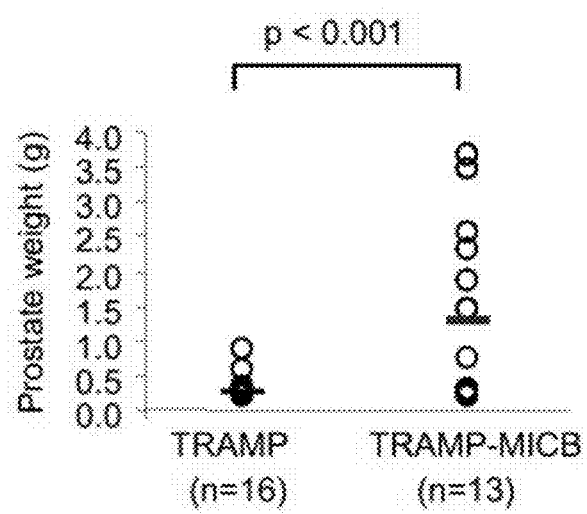
FIGS. 4A-4B demonstrate that expression of the shedding-sensitive native MICB facilitates progression to poorly-differentiated (PD) prostate carcinoma.
Figure 4B:
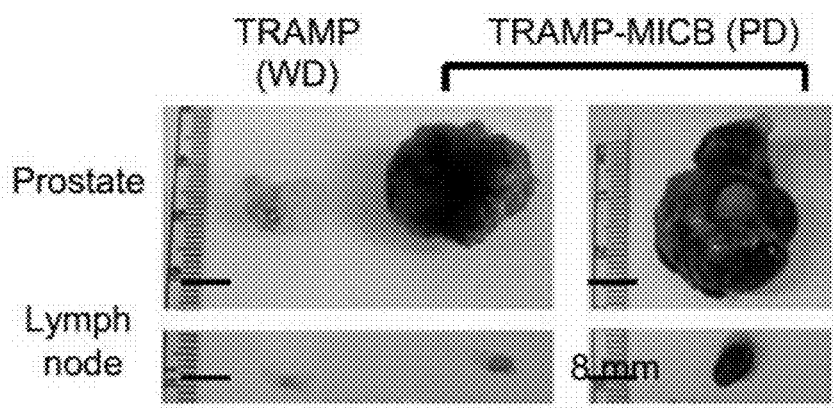

Increased Incidence of Aggressive Carcinomas in TRAMP Mice Expressing Shedding-Sensitive NKG2D Ligand MICB. At 24 weeks of age, 50% (6/12) TRAMP-MICB male mice had palpable large tumors (FIGS. 4A and 4B) and exhibited PD carcinomas[35,36] (Table 1). Of the six smallest TRAMP-MICB tumors, three were well differentiated (WD) carcinomas and three were mildly differentiated (MD) carcinomas (Table 1), a transitional lesion that was characterized by nearly anaplastic sheets of cells with remnants of glandular architecture[35,36]. In comparison, only 12.5% (2/13) of control TRAMP mice had large tumor volumes (defined as prostate weight exceeding mean value by twice of standard error of the mean (SEM)), that were predominantly phylloides-like (PHY) lesions similar to a rare lesion in human prostate cancer with unclear prognosis (Table 1) characterized by staghorn luminal patterns[35]. Furthermore, all six of the TRAMP-MICB mice that developed PD carcinomas had metastatic disease as confirmed by immunostaining for the SV40T oncoprotein; five had massive metastatic deposits in the pelvic lymph nodes (data not shown) and one had a lung metastasis (data not shown). In comparison, only one out of 13 age-matched TRAMP controls had evidence of metastatic disease (data not shown).

To better understand the role of the shedding-sensitive native NKG2D ligand in disease progression, tumor incidence and pathological characteristics in cohorts of TRAMP-MICB and TRAMP mice were compared at 8, 12, and 16 weeks of age (Table 1). At 8 weeks of age, all the TRAMP-MICB and TRAMP mice developed PIN-like lesions in the prostate. At 12 weeks of age, all the TRAMP-MICB but only 69.2% (9/13) of TRAMP mice displayed evidence of carcinoma in the prostate. At 16 weeks of age, all the TRAMP and TRAMP-MICB mice developed prostate carcinoma but 40% (4/10) of TRAMP-MICB mice had evidence of MD lesions whereas only well-differentiated carcinomas were identified in the prostate of TRAMP mice. Together, these data indicate that expression of the shedding-sensitive native MICB in the prostate epithelium facilitates earlier initiation and progression of prostate carcinoma.

Figures 5A, 5B, 5C, 5D, 5E:
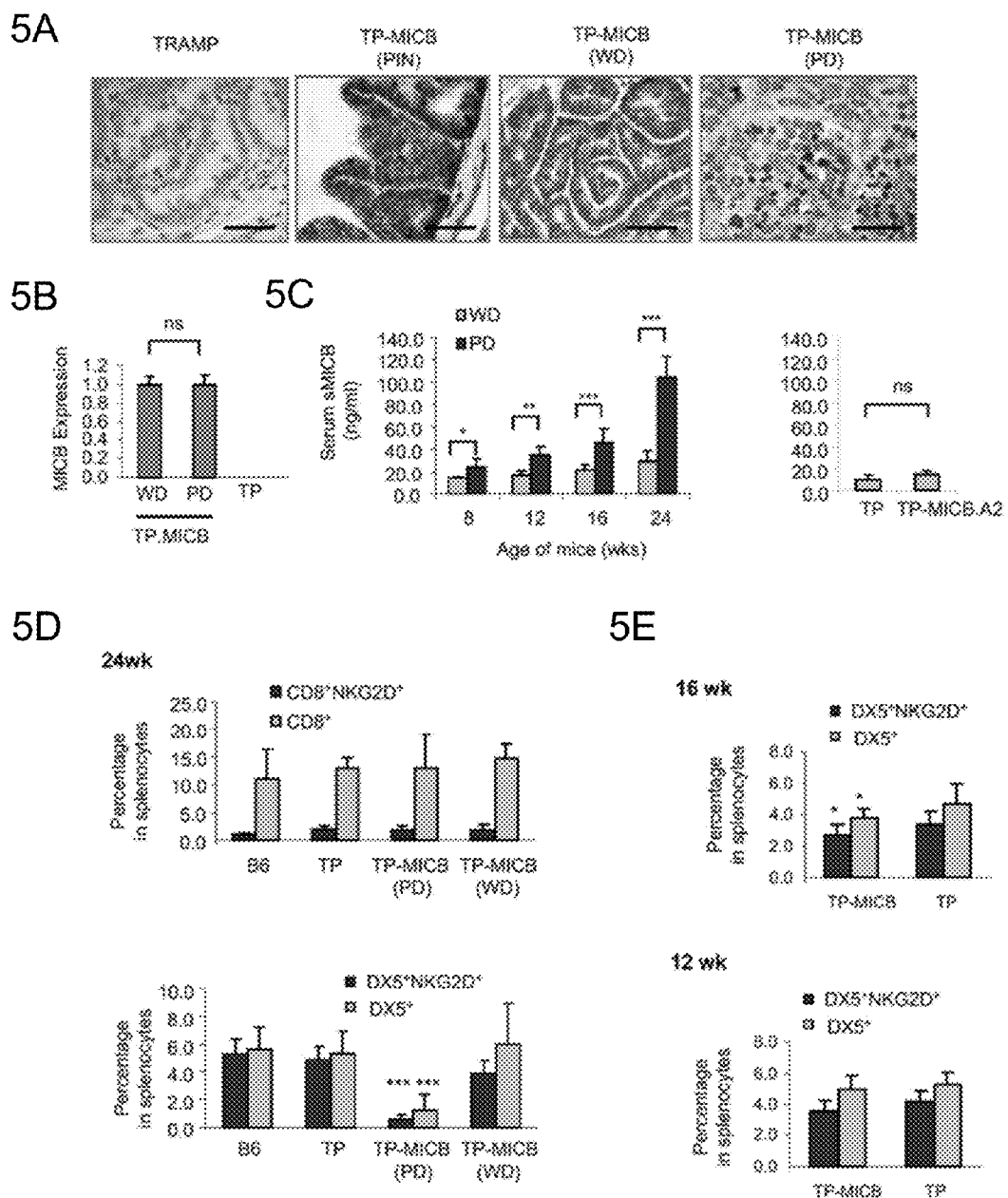
FIGS. 5A-5E demonstrate that soluble but not membrane-bound MICB impairs NKG2D-mediated NK cell immunity and contributes to the progression to PD carcinomas.

Progression to PD Carcinoma in TRAMP-MICB Mice is Associated with Elevated Tumor Shedding of sMICB. To address whether the progression to PD carcinomas in TRAMP-MICB mice is due to chronic exposure to cell surface membrane-bound MICB or tumor shedding of sMICB, MICB expression was examined in tumor lesions from TRAMP-MICB mice by immunohistochemistry with 6D4.6, an antibody specific for the α1α2 ectodomain of MICA and MICB[8,16]. As shown representatively in FIG. 5A, little or no cell surface MICB expression was detected in PD lesions in TRAMP-MICB in comparison to the levels detected in WD or PIN-like lesions. Conversely, intense MIC immunostaining in the PD lesions was seen in the interstitial space (FIG. 5A, arrow). This pattern of surface MICB expression in PD and WD carcinomas is similar to the inventors' previous observation of MIC expression in high grade and low grade prostate carcinomas in cancer patients[22]. Furthermore, semiquantitative RT-PCR did not reveal a significant difference of MICB expression in PD and WD lesions at the transcriptional level (FIG. 5B), suggesting that the reduced levels of detected MICB protein in the PD lesions was due to modification of MICB expression at the post-transcriptional level. Indeed, a profoundly elevated level of sMICB was detected in serum of TRAMP-MICB mice that developed PD lesions at 24-week of age (FIG. 5C). Also, measurement of serum levels of sMICB from individual TRAMP-MICB animal during carcinoma development in the 24-week cohort revealed that sMICB was detected in all TRAMP-MICB mice with levels that increased as the animals aged (FIG. 5C). Strikingly, mice that developed PD tumors by 24 weeks of age had the highest levels of serum sMICB compared to those developed WD tumors, with a pronounced elevation by 24 weeks of age (FIG. 5C, $p<0.01$). Together, these data clearly demonstrate that the progression to PD carcinomas in TRAMP-MICB mice was not due to chronic exposure to tumor cell surface membrane-bound MICB, but was associated with loss of tumor surface MICB and elevated serum levels of sMICB.

Figure 7A:
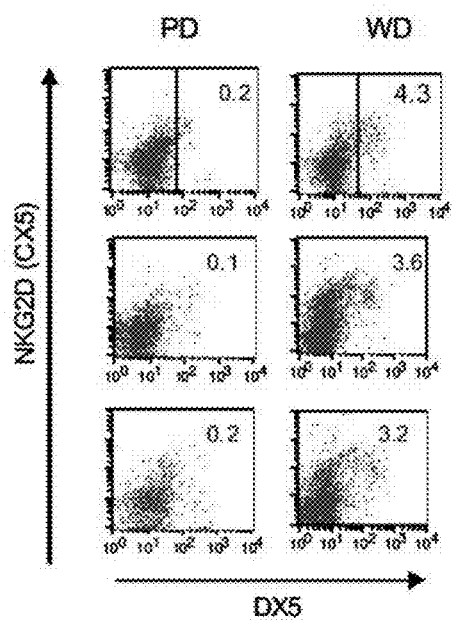
FIGS. 7A-7B depicts the results of representative flow cytometry analyses of NKG2D expression on splenic NK (CD3−DX5+) and CD3− CD8+ T cells from the 24-week cohort of TRAMP-MICB mice. Numbers denote percentage of NKG2D+ DX5+ (A) or NKG2D+ CD8+ cell population in splenocytes. PD, mice that development PD carcinomas. WD, mice that developed WD carcinomas.
Figure 7B:
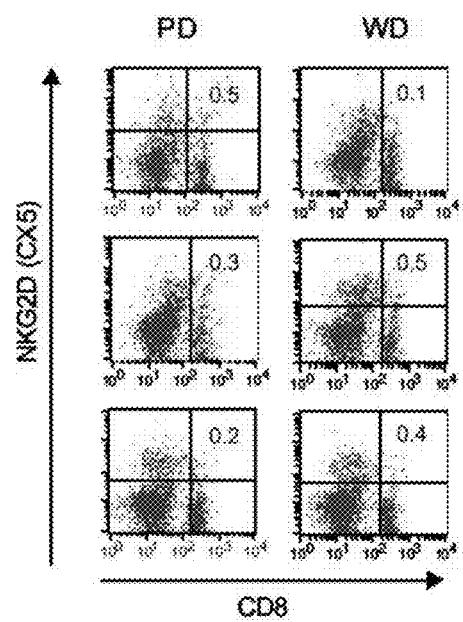

To further address how elevated serum sMICB may facilitate the development of PD tumors, the relevance of NKG2D expression on splenic CD8 T and NK cells as a function of the development of PD tumors in TRAMP-MICB mice was examined. At the age of 24 weeks, all the TRAMP-MICB and TRAMP mice demonstrated similar levels of splenic CD8 T cell populations. However, only a small fraction (8-10%) of the CD8 T cells expressed NKG2D that were not significantly different than TRAMP-MICB and TRAMP mice (FIG. 5D). Given that NKG2D is only expressed by activated mouse CD8 T cells and that antigen-specific CD8 T cell tolerance is well-documented in TRAMP mice[37, 38], this observation would be not unexpected. Intriguingly, splenic NK cell populations showed markedly variation by DX5 staining within the 24-week cohort of TRAMP-MICB mice. Animals that developed PD carcinomas not only had a diminished splenic NKG2D+ DX5+ NK cell population ($p<0.001$) in comparison to those that developed WD carcinomas or TRAMP mice, but also had nearly complete loss of the splenic DX5+ NK cell population (FIG. 5D, FIGS. 7A-7B). Analyses of cohorts of TRAMP-MICB mice at the ages of 16 and 12 weeks did not reveal such a dramatic depletion of splenic DX5+ NK cells. However, a significant reduction in both NK and NKG2D+ NK cells was seen in the 16-week cohort of TRAMP-MICB mice in comparison to TRAMP littermates (FIG. 5E). These data suggest that sMICB may directly or indirectly induce depletion of splenic NK cells to compromise NKG2D-mediated NK immunity to facilitate tumor progression. These data also suggest that NK cells may play an essential role in controlling development of PD tumors.

Figure 6:
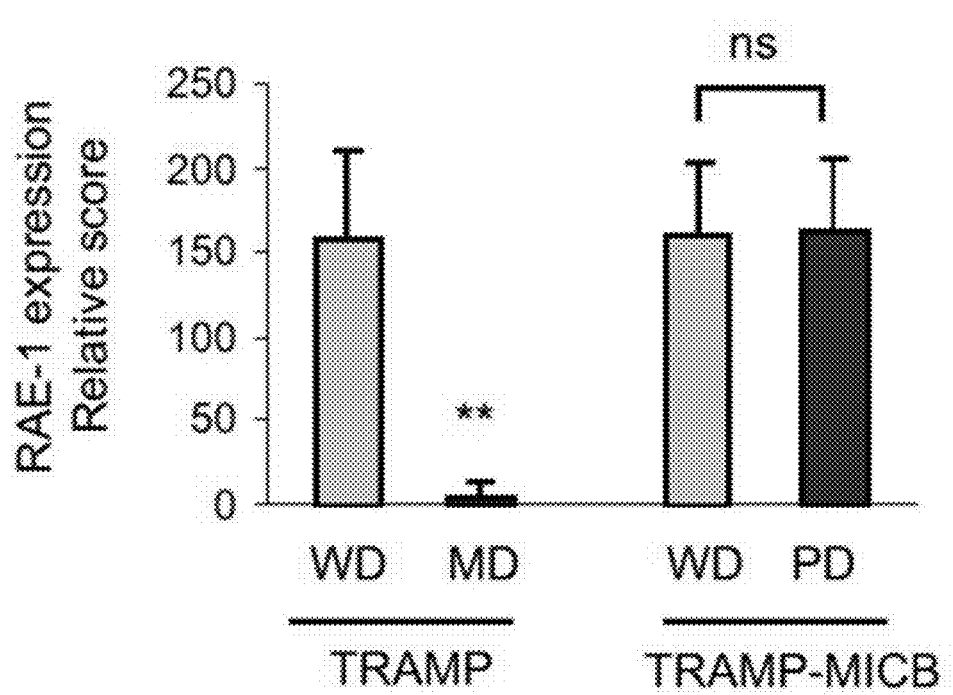
FIG. 6 depicts IHC staining demonstrating a pattern of endogenous NKG2D ligand RAE-1 expression in TRAMP and TRAMP-MICB carcinomas. Data demonstrated consistent RAE-1 expression in PD and WD carcinomas from TRAMP-MICB mice but differential RAE-1 expression in large and small TRAMP tumor. Relative scores of RAE-1 expression in all the samples analyzed from the 24-week cohorts of TRAMP-MICB and TRAMP mice. Data shown represents results from four independent assays.

Development of PD Tumor in TRAMP-MICB Mice is not Associated with Immune Editing of Endogenous Mouse NKG2D Ligand Expression. Guerra et al. have shown that endogenous NKG2D ligand expression in the PD lesions of TRAMP mice was downregulated by functional NKG2D[19], providing an alternative explanation of tumor immunoediting NKG2D function. To address whether immunoediting of endogenous mouse NKG2D ligand expression contributes, at least in part, to the development of PD tumors in TRAMP-MICB mice, the expression of RAE-1, the most abundantly expressed endogenous mouse NKG2D ligand in TRAMP tumors[19] was examined. Consistent with the observation by Guerra et al[19], small tumors from TRAMP mice retained RAE-1 expression, whereas large TRAMP tumors rarely expressed RAE-1 as determined by immunohistochemistry (FIG. 6). Conversely, PD tumors from TRAMP-MICB mice retained similar levels of RAE-1 expression to which in WD tumors from TRAMP-MICB mice or small tumors of TRAMP mice (FIG. 6). This can be attributed to impaired NKG2D expression and lack of NKG2D-mediated negative immunoediting of RAE-1 expression in PD tumors from TRAMP -MICB mice. These observations suggest that PD carcinomas development in TRAMP-MICB mice is not due to immunoediting of endogenous NKG2D ligands, providing further evidence that sMICB-induced deficiency in NKG2D protective function is the major mechanism for progression to advanced carcinomas.

Discussion

A large body of evidence obtained in experimental animal models supports the significance of NKG2D function in tumor immunity. However, previous data has not been able to clarify, whether sustained expression of NKG2D ligands on tumor cells or chronic exposure of NKG2D to its ligands expressed on tumor cells[30-32] is most beneficial for tumor immunity. To resolve the apparent paradox, double transgenic TRAMP-MICB.A2 and TRAMP-MICB mouse models were established and used to clearly demonstrate that the impact of ligand expression on tumor cells on NKG2D immunity depends on whether the ligand can be sustained as the membrane-restricted form or shed to generate the soluble form. It is demonstrated herein that expression of the membrane-restricted shedding-resistant NKG2D ligand MICB.A2 could sustain NKG2D protective immunity and prevent spontaneous tumorigenesis and that the expression of shedding-sensitive native NKG2D ligand MICB facilitates tumor progression through soluble ligand-mediated suppression of NKG2D function.

Conflicting reports based on in vitro and in vivo studies with limitations have suggested that chronic exposure to membrane-bound ligands also impairs NKG2D function. While the in vitro report was derived from co-culturing mouse NK cells with tumor cells expressing mouse NKG2D ligand RAE-1[31], it was not clear whether the consequence of exposure was due to soluble RAE-1 or membrane-bound RAE-1, as RAE-1 was recently shown to be spontaneously shed by mouse tumor cells[2]. With a different aspect of limitations, the existing conflicting conclusion from in vivo studies was based on enforced constitutive expression of NKG2D ligand on normal mouse[30, 32], not in the context of tissue-specific transformation and thus not resembling the feature of NKG2D ligand expression in cancer patients. For example, one transgenic mouse model that was created by expressing human MICA under the constitutive and ubiquitous mouse MHC class I H-2 Kb promoter on a C57BL.6 background showed impaired ability of NK cells to reject MICA-transfected RMA tumors in comparison to the wild-type counterparts[30]. In other models[32], NKG2D ligand RAE-1ε was expressed in normal mice under the constitutive involucrin promoter (inducing squamous epithelium expression) or the ubiquitous chicken β-actin promoter; local and systemic NKG2D downregulation was noted in these mice in comparison to the wild-type counterparts. Notably, in these transgenic mouse models, NKG2D ligand expression was "ectopic" under the direction of a constitutive or ubiquitous promoter in somatic cells. Given the magnitude of ligand-induced NKG2D signaling on activating NK cell cytoxicity, any down-regulation of NKG2D function may be expected in these transgenic mice in compare to an otherwise wild type counterpart as a self-regulatory mechanism to allow normal embryonic development. Thus, the downregulation of NKG2D by sustained ligand expression in these mouse models may not represent the real situation in cancer patients per se. Distinguishing from these studies, bi-transgenic mice were created in which not only NKG2D ligand and the onco-protein SV40T were concomitantly and specifically induced in the prostate after puberty under the direction of an androgen-sensitive probasin promoter[33], but also the shedding-sensitive NKG2D ligand MICB and the shedding-resistance NKG2D ligand MICB.A2 were differentiated expressed. Furthermore, it is demonstrated herein that shedding of the native MICB was concurrent with tumor progression in the TRAMP-MICB mice as has been shown in many types of human malignacies[23-27, 29, 40, 41]. Thus, NKG2D ligand expression in our bi-transgenic mice should more closely resemble the incidence observed in human cancers and largely account for the differences between the data described herein and results generated from other animal models[30,32].

While our data is consistent with the observations of Guerra et al[19] demonstrating the significance of NKG2D function in the progression of TRAMP carcinomas, demonstrated herein is that tumor progression to more advanced carcinomas in the TRAMP-MICB mice was associated with shedding of the NKG2D ligand MICB and defective NK cell protective immunity. Along this line, the in vivo NK and CD8 T cell depletion studies in TRAMP-MICB.A2 mice described herein also supported a significant role of NK cell in controlling the progression to advanced tumors. Furthermore, demonstrated herein is that sMICB-induced defect in NK cell immunity was implemented at multiple levels, a depletion of NK cells and the impaired NKG2D expression on the surviving NK cells. Interestingly, MIC (most likely sMIC)-induced NK cell apoptosis and depletion has recently been reported in other types of advanced carcinomas[39]. These findings suggest that NKG2D-based NK cell immunotherapy can be an effective treatment for advanced prostate cancer, and for other types of advanced malignancies as well.

Correlation of elevated serum levels of soluble MIC (A/B) with advanced diseases stages has been well-demonstrated by many studies in cancer patients[23-27, 29, 40, 41]. Similar to clinical observations, demonstrated herein are elevated serum levels of sMICB correlated with development of PD carcinomas in TRAMP-MICB mice. This further supports the utility of the model system described herein to explore the immunology of tumor progression as well as the uniqueness of the model to recapitulate the specific interactions between NKG2D and its cognate ligands during tumor progression. In conclusion, this study not only resolves the controversy over the impact of ligand expression on NKG2D function but also presents a pre-clinical autochthonous mouse model that can be used to develop, credential and refine NKG2D-based immunotherapy applicable for a board range of malignancies.

Experimental Procedures

Mice. Mice were bred and housed under specific pathogen-free conditions in the University of Washington animal facility in accordance with institutional guidelines. All mice used in this study were on the C57BL6 (B6) background. The rPB-MICB and rPB-MICB.A2 expression cassette were constructed by replacing the SV40T fragment from rPB-SV40T expression cassette[33] with the cDNA fragments encoding MICB or MICB.A2 respectively. The construction of cDNA encoding for MICB.A2 has been previously described[16]. The entire rPB-MICB or rPB -MICB.A2 expression cassette was gel isolated following digestion with HindIII and was microinjected into fertilized B6 embryos respectively. Transgenic progeny were identified by PCR analysis of DNA extracted from tail biopsies using the forward primer specific for rPB (5'-acaagtgcatttagcctctccagta-3') (SEQ ID NO:15) and the reverse primer specific for MICB (5'-tgtgtcttggtcttcatggc-3') (SEQ ID NO: 19) or M1CB.A2 (5'-cagagacagcgtggtgagt-catatg-3') (SEQ ID NO: 16). The male rPB-MICB and rPB-MICB.A2 animals were bred with female TRAMP mice to generate the experimental male TRAMP-MICB and TRAMP-MICB.A2 animals. Presence of double transgenes was identified by PCR analysis of DNA extracted from tail biopsies using the primers specific for SV40Tag (Forward 5'-gatatggctgatcatgaacagact-3' (SEQ ID NO: 17) and Reverse 5'-tttgaggatgtaaagggcactg-3' (SEQ ID NO: 18)) and MICB or MICB.A2 as described above. All experimental mice were randomly assigned to cohorts and sacrificed at 10, 12, 16, and 24 weeks of age for evaluation. Prostates, lymph nodes, liver, lung, and femur were collected for histological evaluation. Spleens were collected for immunological evaluation. Blood were collected for assaying serum levels of sMICB by ELISA.

Histological and Immunohistochemical Examination. The mouse prostate and other soft tissues were fixed in 10% formaldehyde and embedded in paraffin wax. The bone tissues were de-calcificated for 24 h before embedded. Five-micrometer sections were cut and stained with H&E for pathological evaluation. Sections were also stained with: 1) anti-MICB (and MICB.A2) mAb 6D4.6 (mouse IgG; 1:500; Biolegend); 2) anti-panRAE-1 antibody (Rat mAb IgG2a; 1:500; R&D); 3) anti-SV40T antigen (Rabbit polyclonal IgG, 1:200; Santa Cruz); 4) anti-mouse p63 antibody (Mouse mAb IgG2a; 1:200; Thermo Scientific). Sections were deparaffinized, incubated for 10 min in 10 mM citrate buffer (pH 6.0) at 95° C. for antigen retrieval. Endogenous peroxidase activity was quenched with 3% hydrogen peroxide. After quenching endogenous peroxidase activity and blocking nonspecific binding, slides were incubated with specific primary antibody overnight at 4C followed by subsequent incubation with the appropriate biotinylated secondary antibody: goat anti-rabbit IgG (Vector, Burlingame, Calif.); rabbit anti-rat IgG (Vector); goat anti-mouse IgG (Vector) at a 1:1000 dilution for 20 minutes at 37° C. Immunoreactive antigens were detected using the Vectastain Elite ABC Immunoperoxidase Kit and DAB. All slides were counterstained with hematoxylin (Vector) and mounted with Permount (Fisher Scientific). Immunostaining was assessed using a quasi-continuous score, created by multiplying each intensity level (0 for no stain, 1 for faint/equivocal stain, and 2 for intense stain) by the corresponding percentage of cells in the slide staining at that intensity and summing the results.

Pathological Evaluation. Ten randomly selected fields of H&E-stained sections of the prostate lobes from individual mouse of each cohort were independently scored by two scientists for incidence and percentage of area corresponding to each pathologic stage. Pathologic grading wasp erformed according to the recommendations of published studies[33,35].

In Vivo Depletion of NK and CD8 T Cells. Cohorts of 14 to 16-week-old of TRAMP-MICB.A2 male mice were injected i.p. with purified anti-NK1.1 (PK136) or anti-CD8 (clone 2.43) antibody (both from Bioxcell, Lebanon, N.H.). Antibodies were injected i.p. twice weekly at the dose of 100 μg/animal for two weeks then once weekly for additional 6 weeks to maintain the depletion status. Mice received irrelevant mouse IgG or rat IgG as isotype controls. These depletion conditions were validated by flow cytometry analysis of splenocytes using phycoerythrin-conjugated anti-CD49b (Pharmingen) or anti-CD8α (PharMingen) that were non-competing with the above antibodies used for in vivo depletion; 95% of the relevant cell subset was depleted, whereas all of the other subsets remained within normal levels (data not shown).

Flow Cytometry Analysis. Single cell suspensions of splenocytes were prepared as described[16]. Cells were incubated on ice for 30 min with a combination of FITC -conjugated mAb DX5 or anti-mCD8 antibody (ebiosciences), PE-conjugated anti-mouse NKG2D mAb CX5 (ebioscience), and PerCP-conjugated anti-mouse CD3 antibody (eiosciences) and analyzed using a BD FACscan. Data were analyzed using the BD CellQuestPro (BD Biosciences). Cytotoxicity assay. Pooled splenocytes from two to three representative mice with similar prostate disease progression within the same experimental group were used as effectors in a standard 4-hour $^{51}$Cr release assay as described previously[16]. The $^{51}$Cr-labeled TRAMP-MICB.A2 cells were used as target cells. 10 µg/ml of anti-NKG2D antibody C7 (ebioscience) was for blocking NKG2D function. Incubated on ice for 30 min[16] ELISA for sMICB. Serum was diluted 1:2 with PBS. Amount of soluble MICB was measured using human MICB DuoSet sandwich ELISA kit (R&D Systems) as previously described.

Statistical Analysis. Difference between means of populations was compared by standard Student's t-test for unpaired, one-tailed samples. A p value of 0.05 or less was considered significant.

References

1. Nausch, N. & Cerwenka, A. NKG2D ligands in tumor immunity. Oncogene 27, 5944-5958 (2008).
2. Champsaur, M. & Lanier, L. L. Effect of NKG2D ligand expression on host immune responses. Immunol Rev 235, 267-285 (2010).
3. Bauer, S. et al. Activation of NK cells and T cells by NKG2D, a receptor for stress-inducible MICA. Science 285, 727-729 (1999).
4. Groh, V. et al. Costimulation of CD8alphabeta T cells by NKG2D via engagement by MIC induced on virus-infected cells. Nat Immunol 2, 255-260 (2001).
5. Girlanda, S. et al. MICA expressed by multiple myeloma and monoclonal gammopathy of undetermined significance plasma cells Costimulates pamidronate-activated gammadelta lymphocytes. Cancer Res 65, 7502-7508 (2005).
6. Wu, J., Groh, V. & Spies, T. T cell antigen receptor engagement and specificity in the recognition of stress-inducible MHC class I-related chains by human epithelial gamma delta T cells. J Immunol 169, 1236-1240 (2002).
7. Wu, J. et al. An activating immunoreceptor complex formed by NKG2D and DAP10. Science 285, 730-732 (1999).
8. Groh, V. et al. Broad tumor-associated expression and recognition by tumor-derived gamma delta T cells of MICA and MICB. Proc Natl Acad Sci USA 96, 6879-6884 (1999).
9. Sutherland, C. L., Chalupny, N.J. & Cosman, D. The UL16-binding proteins, a novel family of MHC class I-related ligands for NKG2D, activate natural killer cell functions. Immunol Rev 181, 185-192 (2001).
10. Cosman, D. et al. ULBPs, novel MHC class I-related molecules, bind to CMV glycoprotein UL16 and stimulate NK cytotoxicity through the NKG2D receptor. Immunity 14, 123-133 (2001).
11. Diefenbach, A., Jensen, E. R., Jamieson, A. M. & Raulet, D. H. Rae1 and H60 ligands of the NKG2D receptor stimulate tumour immunity. Nature 413, 165-171 (2001).
12. Cerwenka, A., Baron, J. L. & Lanier, L. L. Ectopic expression of retinoic acid early inducible-1 gene (RAE-1) permits natural killer cell-mediated rejection of a MHC class I-bearing tumor in vivo. Proc Natl Acad Sci USA 98, 11521-11526 (2001).
13. Carayannopoulos, L. N., Naidenko, O. V., Fremont, D. H. & Yokoyama, W. M. Cutting edge: murine UL16-binding protein-like transcript 1: a newly described transcript encoding a high-affinity ligand for murine NKG2D. J Immunol 169, 4079-4083 (2002).
14. Diefenbach, A., Hsia, J. K., Hsiung, M. Y. & Raulet, D. H. A novel ligand for the NKG2D receptor activates NK cells and macrophages and induces tumor immunity. Eur J Immunol 33, 381-391 (2003).
15. Dunn, C. et al. Human cytomegalovirus glycoprotein UL16 causes intracellular sequestration of NKG2D ligands, protecting against natural killer cell cytotoxicity. J Exp Med 197, 1427-1439 (2003).
16. Wu, J. D., Atteridge, C. L., Wang, X., Seya, T. & Plymate, S. R. Obstructing shedding of the immunostimulatory MHC class I chain-related gene B prevents tumor formation. Clin Cancer Res 15, 632-640 (2009).
17. Diefenbach, A., Jamieson, A.M., Liu, S.D., Shastri, N. & Raulet, D. H. Ligands for the murine NKG2D receptor: expression by tumor cells and activation of NK cells and macrophages. Nat Immunol 1, 119-126 (2000).
18. Friese, M. A. et al. MICA/NKG2D-mediated immunogene therapy of experimental gliomas. Cancer Res 63, 8996-9006 (2003).
19. Guerra, N. et al. NKG2D-deficient mice are defective in tumor surveillance in models of spontaneous malignancy. Immunity 28, 571-580 (2008).
20. Smyth, M. J. et al. NKG2D function protects the host from tumor initiation. J Exp Med 202, 583-588 (2005).
21. Groh, V., Wu, J., Yee, C. & Spies, T. Tumour-derived soluble MIC ligands impair expression of NKG2D and T-cell activation. Nature 419, 734-738 (2002).
22. Wu, J. D. et al. Prevalent expression of the immunostimulatory MHC class I chain-related molecule is counteracted by shedding in prostate cancer. J Clin Invest 114, 560-568 (2004).
23. Jinushi, M. et al. MHC class I chain-related protein A antibodies and shedding are associated with the progression of multiple myeloma. Proc Natl Acad Sci USA 105, 1285-1290 (2008).
24. Rebmann, V. et al. Soluble MICA as an independent prognostic factor for the overall survival and progression-free survival of multiple myeloma patients. Clin Immunol 123, 114-120 (2007).
25. Tamaki, S. et al. Soluble MICB serum levels correlate with disease stage and survival rate in patients with oral squamous cell carcinoma. Anticancer. Res 30, 4097-4101 (2010).
26. Holdenrieder, S. et al. Soluble MICB in malignant diseases: analysis of diagnostic significance and correlation with soluble MICA. Cancer Immunol Immunother 55, 1584-1589 (2006).
27. Holdenrieder, S. et al. Soluble MICA in malignant diseases. Int J Cancer 118, 684-687 (2006).
28. Marten, A., von Lilienfeld-Toal, M., Buehler, M. W. & Schmidt, J. Soluble MIC is elevated in the serum of patients with pancreatic carcinoma diminishing gammadelta T cell cytotoxicity. Int J Cancer 119, 2359-2365 (2006).
29. Tamaki, S. et al. Association between soluble MICA levels and disease stage 1V oral squamous cell carcinoma in Japanese patients. Hum Immunol 69, 88-93 (2008).
30. Wiemann, K. et al. Systemic NKG2D down-regulation impairs NK and CD8 T cell responses in vivo. J Immunol 175, 720-729 (2005).
31. Coudert, J. D. et al. Altered NKG2D function in NK cells induced by chronic exposure to NKG2D ligand-expressing tumor cells. Blood 106, 1711-1717 (2005).
32. Oppenheim, D. E. et al. Sustained localized expression of ligand for the activating NKG2D receptor impairs natural cytotoxicity in vivo and reduces tumor immunosurveillance. Nat Immunol 6, 928-937 (2005).

33. Greenberg, N. M. et al. Prostate cancer in a transgenic mouse. Proc Natl Acad Sci USA 92, 3439-3443 (1995).
34. Degrassi, A. et al. Magnetic resonance imaging and histopathological characterization of prostate tumors in TRAMP mice as model for pre-clinical trials. Prostate 67, 396-404 (2007).
35. Kaplan-Lefko, P. J. et al. Pathobiology of autochthonous prostate cancer in a pre -clinical transgenic mouse model. Prostate 55, 219-237 (2003).
36. Gingrich, J. R., Barrios, R. J., Foster, B. A. & Greenberg, N. M. Pathologic progression of autochthonous prostate cancer in the TRAMP model. Prostate Cancer Prostatic Dis 2, 70-75 (1999).
37. Anderson, M. J., Shafer-Weaver, K., Greenberg, N.M. & Hurwitz, A. A. Tolerization of tumor-specific T cells despite efficient initial priming in a primary murine model of prostate cancer. J Immunol 178, 1268-1276 (2007).
38. Bai, A., Higham, E., Eisen, H. N., Wittrup, K. D. & Chen, J. Rapid tolerization of virus-activated tumor-specific CD8+ T cells in prostate tumors of TRAMP mice. Proc Natl Acad Sci USA 105, 13003-13008 (2008).
39. Sconocchia, G. et al. Defective infiltration of natural killer cells in MICA/B -positive renal cell carcinoma involves beta(2)-integrin-mediated interaction. Neoplasia 11, 662-671 (2009).
40. Doubrovina, E. S. et al. Evasion from NK cell immunity by MHC class I chain-related molecules expressing colon adenocarcinoma. J Immunol 171, 6891-6899 (2003).
41. Duan, X. et al. Clinical significance of the immunostimulatory MHC class I chain -related molecule A and NKG2D receptor on NK cells in pancreatic cancer. Med Oncol (2010).

Example 2

Figure 8A:
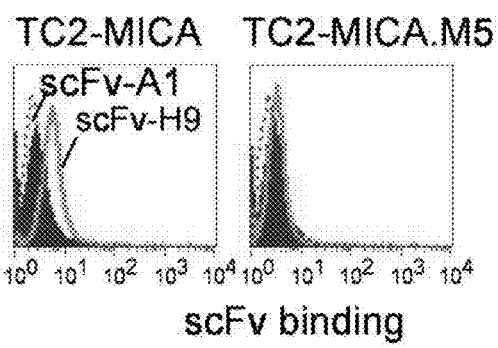
FIGS. 8A-8D demonstrate that a phage antibody scFv-H9 inhibits MIC shedding and makes tumor cells more sensitive to NK cell killing.

Single-Chain Fragment Antibody scFv-H9 from a Phage Display Library Screened Against the 6-aa Motif can Inhibit MIC Shedding and Increase Tumor Cell Sensitivity to NK Cell Killing A phage display scFv library of 2.8×10$^8$ complexity was screened with the peptides composed of the 6-aa motif as antigens. After four rounds of panning with the biotinylated peptides, we identified a scFv phage clone, scFv-H9 that binds to TRAMP-C2-MICA cells but not to TRAMP-C2-MICA-M5 cells (FIG. 8A). TRAMP-C2-MICA-M5 cells express a shedding-resistant version of MIC mutated such that the epitope comprised of the amino acid sequence of SEQ ID NO: 1 is not present (see, e.g. Wang et al. Biochem Biophys Res Commun 2009 387:476-481)

Figure 8B:
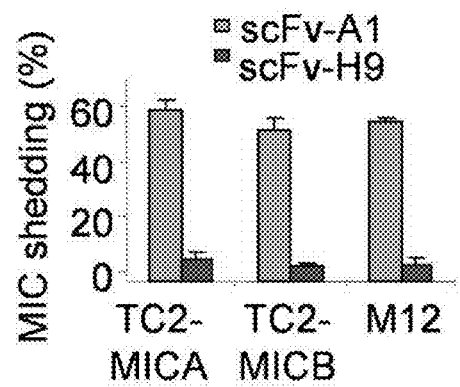
Figure 8C:
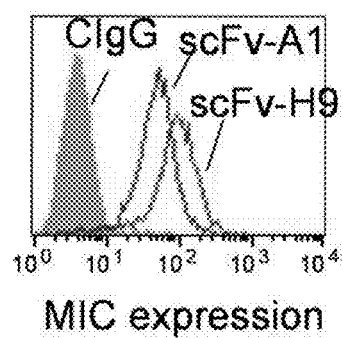
Figure 8D:
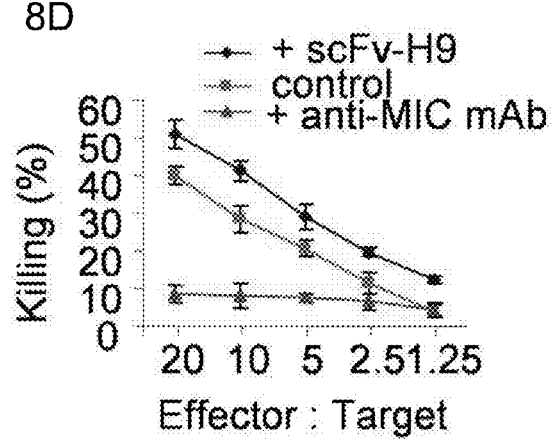

The scFv-H9 can inhibit both MICA and MICB shedding by 90% in vitro (FIG. 8B). It is demonstrated herein that treatment with scFv-H9 increases cell surface MIC expression (FIG. 8C) and that binding of the scFv-H9 to MIC did not interfere with the recognition of MIC by NK cells (FIG. 8D).

Administration of an antibody or antigen-binding portion thereof comprising the CDRs of ScFv-H9 or conservative substitution variants thereof that maintain specific binding to TRAMP-C2-MIC cells but not to TRAMP-C2_MIC-M5 cells can be used to reduce MIC shedding in vivo, stimulate or increase NKG2D-mediated tumor cell killing, and treat MIC positive cancers.

References Relating To Antibody Domains

1. Kabat, E. A. et al. (1991) Sequences of proteins of immunological interest, 5th ed. (Bethesda: US Department of Health and Human Services, Public Health Service, National Institutes of Health, NIH Publication No. 91-3242).
2. Abhinandan, K. R. and Martin, A. C. R. (2008) Analysis and improvements to Kabat and structurally correct numbering of antibody variable domains Molecular Immunology, 45, 3832-3839.
3. MacCallum, R. M., Martin, A. C. R. and Thornton, J. T. Antibody-antigen interactions: Contact analysis and binding site topography. J. Mol. Biol. 262, 732-745.
4. Altschul, Stephen F., Thomas L. Madden, Alejandro A. Schäffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402.

The references cited herein and throughout the specification are incorporated herein by reference in their entirety.

TABLE 1

Pathologic comparison of TRAMP and TRAMP-MICB mice.

| Age (wks) | Pathology | TRAMP | TRAMP-MICB |
|---|---|---|---|
| 8 | PIN | 12/12 (100%) | 12/12 (100%) |
|  | Tumor | 0 | 0 |
|  | $^a$Prostate weight | 0.09 ± 0.00 | 0.09 ± 0.00 |
| 12 | PIN | 4/13 (30.8%) | 0/10 (0%) |
|  | Tumor | 9/13 (69.2%) | 10/10 (100%) |
|  | WD | 9/9 (100%) | 7/10 (70%) |
|  | MD | 0 | 3/10 (30%) |
|  | Prostate weight | 0.13 ± 0.00 | 0.16 ± 0.01 |
| 16 | Tumor | 15/17 (88.2%) | 10/10 (100%) |
|  | PIN | 2/17 (11.8) | 0 |
|  | WD | 15/15 (100%) | 4/10 (40%) |
|  | $^b$MD | 0 | 6/10 (60%) |
|  | Prostate weight | 0.17 ± 0.01 | 0.20 ± 0.01 |
| 24 | PIN | 0/13 | 0/12 |
|  | Tumor | 13/13 | 12/12 |
|  | WD | 12/13 (91.7%) | 3/12 (25%) |
|  | PD | 0/13 | 6/12 (50%) |
|  | MD | 1/13 | 3/12 (25%) |
|  | $^c$Phylloides | 2/13 (12.5%) | 0/13 |
|  | Metastasis | 1/13 (7.6%) | 6/12 (50%) |
|  | Prostate weight | 0.30 ± 0.04 | 0.82 ± 0.29 |

$^a$expressed as Mean ± SEM (g).
$^b$MD lesions are in transition to PD lesions.
$^c$the two phylloides, one is a MD lesion and the other is a WD lesion.

SEQUENCE LISTING

SEQ ID NO: 01
NGTYQT

SEQ ID NO: 02  Light chain CDR1 of ScFv-H9 (Kabat)
QASQDIGNNLI

SEQ ID NO: 03  Light chain CDR2 of ScFV-H9 (Kabat)
YATNLAN

SEQUENCE LISTING

SEQ ID NO: 04  Light Chain CDR3 of ScFV-H9 (Kabat)
QQWSSNP

SEQ ID NO: 05  Heavy Chain CDR1 of ScFV-H9 (Kabat)
NYYMS

SEQ ID NO: 06  Heavy Chain CDR2 of ScFV-H9 (Kabat)
NIYGGNGGTGYNQKFKG

SEQ ID NO: 07  Heavy Chain CDR3 of ScFV-H9 (Kabat)
GDLYAMDY

SEQ ID NO: 08  ScFv-H9
MAQVQLQQSGAELVKPGASVKLSCKTSGYTFSNYYMSWLKQMP
GQNIEWIGNIYGGNGGTGYNQKFKGKATLTVDKSSSTAYMQLSS
LTSEDSAVYFCARGDLYAMDYWGQGTTVTVSSGGGGSGGGGSG
GGGSDIVLTQSPSSMSASLGDRVTITCQASQDIGNNLIWFQQKPG
KSPRPMIYYATNLANGVPSRFSGSGSGTSYSLTISSMEAEDAATY
YCQQWSSNPYTFGGGTKLEIKRAAA

SEQ ID NO: 09  Heavy Chain sequence of ScFV-H9
AELVKPGASVKLSCKTSGYTFSNYYMSWLKQMPGQNIEWIGNIY
GGNGGTGYNQKFKGKATLTVDKSSSTAYMQLSSLTSEDSAVYFC
ARGDLYAMDYWGQGTTVT SEQ ID NO: 10  Light Chain sequence of ScFV-H9
VLTQSPSSMSASLGDRVTITCQASQDIGNNLIWFQQKPGKSPRPM
IYYATNLANGVPSRFSGSGSGTSYSLTISSMEAEDAATYYCQQW
SSNPYTFGG SEQ ID NO: 11  MIC epitope
QTWVATR SEQ ID NO: 12  MIC epitope
YQTWVATR SEQ ID NO: 13  MIC epitope
TWVA SEQ ID NO: 14  MIC epitope
TQQWGDVLPDGNGTYQTWVATR SEQ ID NO: 15  Forward rPB primer
acaagtgcatttagcctctccagta SEQ ID NO: 16  reverse MICB.A2 primer
cagagacagcgtggtgagtcatatg SEQ ID NO: 17  forward SV40Tag primer
Gatatggctgatcatgaacagact SEQ ID NO: 18  reverse SV40Tag primer
tttgaggatgtaaagggcactg SEQ ID NO: 19  reverse MICB primer
tgtgtcttggtcttcatggc

What is claimed:

1. An isolated antibody or antigen-binding portion thereof that specifically binds a MIC polypeptide, said antibody or antigen-binding portion thereof comprising heavy and light chain complementarity determining regions (CDRs):
    (a) a light chain CDR1 having the amino acid sequence of SEQ ID NO: 2;
    (b) a light chain CDR2 having the amino acid sequence of SEQ ID NO: 3;
    (c) a light chain CDR3 having the amino acid sequence of SEQ ID NO: 4;
    (d) a heavy chain CDR1 having the amino acid sequence of SEQ ID NO: 5;
    (e) a heavy chain CDR2 having the amino acid sequence of SEQ ID NO: 6; and
    (f) a heavy chain CDR3 having the amino acid sequence of SEQ ID NO: 7.

2. The isolated antibody or antigen-binding portion thereof of claim 1, which inhibits MIC shedding.

3. The isolated antibody or antigen-binding portion thereof of claim 1, which when bound to MIC on the surface of a cell, does not decrease recognition of MIC by natural killer (NK) cells by more than 10%.

4. A pharmaceutical composition comprising an antibody or antigen-binding portion thereof of claim 1 and a pharmaceutically acceptable carrier.

5. The isolated antibody or antigen-binding portion thereof of claim 1, wherein the antibody or polypeptide is selected from the group consisting of:
    an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, and a bispecific antibody.

6. The isolated antibody or antigen-binding portion thereof of claim 1, which comprises an scFV comprising the amino acid sequence of SEQ ID NO: 8.

7. An isolated antibody or antigen-binding portion thereof that specifically binds an epitope comprising the amino acid sequence NGTYQT (SEQ ID NO: 01) in a MIC polypeptide, said antibody or antigen-binding portion thereof comprising heavy chain CDRs having the amino acid sequences of SEQ ID NO: 5, 6 and 7, said antibody or antigen-binding portion thereof inhibiting MIC shedding.

8. The isolated antibody or antigen-binding portion thereof of claim 7, which comprises light chain CDRs having the amino acid sequences of SEQ ID NOs 2, 3, and 4.

9. The isolated antibody or antigen-binding portion thereof of claim 7, which comprises a heavy chain comprising the amino acid sequence of SEQ ID NO: 09.

10. The isolated antibody or antigen-binding portion thereof of claim 7, which comprises a light chain comprising the amino acid sequence of SEQ ID NO: 10.

11. An isolated antibody or antigen-binding portion thereof that specifically binds an epitope comprising the amino acid sequence NGTYQT (SEQ ID NO: 01) in a MIC polypeptide, said antibody or antigen-binding portion thereof comprising light chain CDRs having the amino acid sequences of SEQ ID NO: 2, 3 and 4, said antibody or antigen-binding portion thereof inhibiting MIC shedding.

12. The isolated antibody or antigen-binding portion thereof of claim 11, which comprises heavy chain CDRs having the amino acid sequences of SEQ ID NO: 5, 6 and 7.

13. The isolated antibody or antigen-binding portion thereof of claim 11, which comprises a light chain comprising the amino acid sequence of SEQ ID NO: 10.

14. The isolated antibody or antigen-binding portion thereof of claim 11, which comprises a heavy chain comprising the amino acid sequence of SEQ ID NO: 09.

15. A method of inhibiting MIC shedding by a cell, the method comprising contacting the cell with an antibody antigen-binding portion thereof of claim 1.

16. The method of claim 15, wherein the cell is an MIC positive epithelial tumor cell or a MIC positive cell of a hematopoietic malignancy.

17. A method of increasing surface MIC expression on a tumor cell, the method comprising contacting the cell with an antibody antigen-binding portion thereof of claim 1.

18. The method of claim 17, wherein the cell is a MIC positive epithelial tumor cell or a MIC positive cell of a hematopoietic malignancy.

19. A method of treating a MIC positive epithelial cell tumor or a MIC positive hematopoietic malignancy in a subject, the method comprising administering an antibody or antigen binding portion thereof of claim 1 to the subject.

20. A cDNA encoding an antibody or antigen-binding portion thereof of claim 1.

* * * * *

SEQUENCE LISTING

<160> NUMBER OF SEQ ID NOS: 22

<210> SEQ ID NO 1
<211> LENGTH: 6
<212> TYPE: PRT
<213> ORGANISM: Homo sapiens

<400> SEQUENCE: 1

Asn Gly Thr Tyr Gln Thr
1               5

```
<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gln Ala Ser Gln Asp Ile Gly Asn Asn Leu Ile
1               5                   10

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Ala Thr Asn Leu Ala Asn
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Gln Trp Ser Ser Asn Pro
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asn Tyr Tyr Met Ser
1               5

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asn Ile Tyr Gly Gly Asn Gly Gly Thr Gly Tyr Asn Gln Lys Phe Lys
1               5                   10                  15

Gly

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 7

Gly Asp Leu Tyr Ala Met Asp Tyr
1               5

<210> SEQ ID NO 8
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Ala Gln Val Gln Leu Gln Gln Ser Gly Ala Glu Leu Val Lys Pro
1               5                   10                  15

Gly Ala Ser Val Lys Leu Ser Cys Lys Thr Ser Gly Tyr Thr Phe Ser
            20                  25                  30

Asn Tyr Tyr Met Ser Trp Leu Lys Gln Met Pro Gly Gln Asn Ile Glu
        35                  40                  45

Trp Ile Gly Asn Ile Tyr Gly Gly Asn Gly Gly Thr Gly Tyr Asn Gln
    50                  55                  60

Lys Phe Lys Gly Lys Ala Thr Leu Thr Val Asp Lys Ser Ser Ser Thr
65                  70                  75                  80

Ala Tyr Met Gln Leu Ser Ser Leu Thr Ser Glu Asp Ser Ala Val Tyr
                85                  90                  95

Phe Cys Ala Arg Gly Asp Leu Tyr Ala Met Asp Tyr Trp Gly Gln Gly
            100                 105                 110

Thr Thr Val Thr Val Ser Ser Gly Gly Gly Ser Gly Gly Gly Gly
        115                 120                 125

Ser Gly Gly Gly Ser Asp Ile Val Leu Thr Gln Ser Pro Ser Ser
    130                 135                 140

Met Ser Ala Ser Leu Gly Asp Arg Val Thr Ile Thr Cys Gln Ala Ser
145                 150                 155                 160

Gln Asp Ile Gly Asn Asn Leu Ile Trp Phe Gln Gln Lys Pro Gly Lys
                165                 170                 175

Ser Pro Arg Pro Met Ile Tyr Tyr Ala Thr Asn Leu Ala Asn Gly Val
            180                 185                 190

Pro Ser Arg Phe Ser Gly Ser Gly Ser Gly Thr Ser Tyr Ser Leu Thr
        195                 200                 205

Ile Ser Ser Met Glu Ala Glu Asp Ala Ala Thr Tyr Tyr Cys Gln Gln
    210                 215                 220

Trp Ser Ser Asn Pro Tyr Thr Phe Gly Gly Gly Thr Lys Leu Glu Ile
225                 230                 235                 240

Lys Arg Ala Ala Ala
                245

<210> SEQ ID NO 9
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ala Glu Leu Val Lys Pro Gly Ala Ser Val Lys Leu Ser Cys Lys Thr
1               5                   10                  15

Ser Gly Tyr Thr Phe Ser Asn Tyr Tyr Met Ser Trp Leu Lys Gln Met
            20                  25                  30
```

```
Pro Gly Gln Asn Ile Glu Trp Ile Gly Asn Ile Tyr Gly Gly Asn Gly
            35                  40                  45

Gly Thr Gly Tyr Asn Gln Lys Phe Lys Gly Lys Ala Thr Leu Thr Val
 50                  55                  60

Asp Lys Ser Ser Ser Thr Ala Tyr Met Gln Leu Ser Ser Leu Thr Ser
 65                  70                  75                  80

Glu Asp Ser Ala Val Tyr Phe Cys Ala Arg Gly Asp Leu Tyr Ala Met
                 85                  90                  95

Asp Tyr Trp Gly Gln Gly Thr Thr Val Thr
            100                 105

<210> SEQ ID NO 10
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Val Leu Thr Gln Ser Pro Ser Ser Met Ser Ala Ser Leu Gly Asp Arg
 1               5                  10                  15

Val Thr Ile Thr Cys Gln Ala Ser Gln Asp Ile Gly Asn Asn Leu Ile
            20                  25                  30

Trp Phe Gln Gln Lys Pro Gly Lys Ser Pro Arg Pro Met Ile Tyr Tyr
            35                  40                  45

Ala Thr Asn Leu Ala Asn Gly Val Pro Ser Arg Phe Ser Gly Ser Gly
 50                  55                  60

Ser Gly Thr Ser Tyr Ser Leu Thr Ile Ser Ser Met Glu Ala Glu Asp
 65                  70                  75                  80

Ala Ala Thr Tyr Tyr Cys Gln Gln Trp Ser Ser Asn Pro Tyr Thr Phe
                 85                  90                  95

Gly Gly

<210> SEQ ID NO 11
<211> LENGTH: 7
<212> TYPE: PRT
<213> ORGANISM: Homo sapiens

<400> SEQUENCE: 11

Gln Thr Trp Val Ala Thr Arg
 1               5

<210> SEQ ID NO 12
<211> LENGTH: 8
<212> TYPE: PRT
<213> ORGANISM: Homo sapiens

<400> SEQUENCE: 12

Tyr Gln Thr Trp Val Ala Thr Arg
 1               5

<210> SEQ ID NO 13
<211> LENGTH: 4
<212> TYPE: PRT
<213> ORGANISM: Homo sapiens

<400> SEQUENCE: 13

Thr Trp Val Ala
 1
```

```
<210> SEQ ID NO 14
<211> LENGTH: 22
<212> TYPE: PRT
<213> ORGANISM: Homo sapiens

<400> SEQUENCE: 14

Thr Gln Gln Trp Gly Asp Val Leu Pro Asp Gly Asn Gly Thr Tyr Gln
1               5                   10                  15

Thr Trp Val Ala Thr Arg
            20

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
acaagtgcat ttagcctctc cagta                                         25

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cagagacagc gtggtgagtc atatg                                         25

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gatatggctg atcatgaaca gact                                          24

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tttgaggatg taaagggcac tg                                            22

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tgtgtcttgg tcttcatggc                                               20
```

```
<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Gly Gly Gly Ser
1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 21

His His His His His His
1               5

<210> SEQ ID NO 22
<211> LENGTH: 735
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(735)

<400> SEQUENCE: 22 atg gcc cag gtg caa ctg cag cag tct ggg gct gag ctg gtg aag cct        48
Met Ala Gln Val Gln Leu Gln Gln Ser Gly Ala Glu Leu Val Lys Pro
1               5                   10                  15 ggg gct tca gtg aag ttg tcc tgc aaa act tct ggt tac acc ttc agc        96
Gly Ala Ser Val Lys Leu Ser Cys Lys Thr Ser Gly Tyr Thr Phe Ser
                20                  25                  30 aat tac tat atg agt tgg ttg aag cag atg cct gga cag aat att gag       144
Asn Tyr Tyr Met Ser Trp Leu Lys Gln Met Pro Gly Gln Asn Ile Glu
            35                  40                  45 tgg atc gga aac att tat ggt gga aat ggt ggt act ggc tat aat cag       192
Trp Ile Gly Asn Ile Tyr Gly Gly Asn Gly Gly Thr Gly Tyr Asn Gln
        50                  55                  60 aag ttc aag ggc aag gcc aca ctg aca gta gac aaa tcc tcc agc aca       240
Lys Phe Lys Gly Lys Ala Thr Leu Thr Val Asp Lys Ser Ser Ser Thr
65                  70                  75                  80 gcc tac atg caa ctc agc agc ctg aca tct gag gac tct gcg gtc tac       288
Ala Tyr Met Gln Leu Ser Ser Leu Thr Ser Glu Asp Ser Ala Val Tyr
                85                  90                  95 ttc tgt gca aga ggg gac ctc tat gct atg gac tac tgg ggc caa ggg       336
Phe Cys Ala Arg Gly Asp Leu Tyr Ala Met Asp Tyr Trp Gly Gln Gly
                100                 105                 110 acc acg gtc acc gtc tcc tca ggt gga ggc ggt tca ggc gga ggt ggc       384
Thr Thr Val Thr Val Ser Ser Gly Gly Gly Gly Ser Gly Gly Gly Gly
            115                 120                 125 tct ggc ggt ggc gga tcg gac atc gtg ctg acc cag tct cca tcc tcc       432
Ser Gly Gly Gly Gly Ser Asp Ile Val Leu Thr Gln Ser Pro Ser Ser
        130                 135                 140 atg tct gca tct ctg gga gac aga gtc act att act tgc cag gca agt       480
Met Ser Ala Ser Leu Gly Asp Arg Val Thr Ile Thr Cys Gln Ala Ser
145                 150                 155                 160
```

```
cag gac att ggg aat aat tta atc tgg ttc cag cag aaa cca ggg aaa      528
Gln Asp Ile Gly Asn Asn Leu Ile Trp Phe Gln Gln Lys Pro Gly Lys
            165             170                 175 tct cct agg cct atg att tat tat gca acc aac ttg gca aat ggg gtc      576
Ser Pro Arg Pro Met Ile Tyr Tyr Ala Thr Asn Leu Ala Asn Gly Val
        180             185                 190 cca tca agg ttc agt ggc agt ggg tct ggg acc tct tac tct ctc aca      624
Pro Ser Arg Phe Ser Gly Ser Gly Ser Gly Thr Ser Tyr Ser Leu Thr
        195             200             205 atc agc agc atg gag gct gaa gat gct gcc act tat tac tgc cag cag      672
Ile Ser Ser Met Glu Ala Glu Asp Ala Ala Thr Tyr Tyr Cys Gln Gln
    210             215             220 tgg agt agt aac ccg tac acg ttc gga ggg ggg acc aag ctg gaa ata      720
Trp Ser Ser Asn Pro Tyr Thr Phe Gly Gly Gly Thr Lys Leu Glu Ile
225             230                 235                     240 aaa cgg gcg gcc gca                                                  735
Lys Arg Ala Ala Ala
            245
```